(12) United States Patent
Dupree et al.

(10) Patent No.: US 6,192,266 B1
(45) Date of Patent: Feb. 20, 2001

(54) SYSTEMS AND METHODS FOR CONTROLLING THE USE OF DIAGNOSTIC OR THERAPEUTIC INSTRUMENTS IN INTERIOR BODY REGIONS USING REAL AND IDEALIZED IMAGES

(75) Inventors: Daniel A. Dupree, Saratoga; Tuan Nguyen, San Jose; Dorin Panescu, Sunnyvale; James G. Whayne, Saratoga, all of CA (US)

(73) Assignee: Boston Scientific Corporation, San Jose, CA (US)

( * ) Notice: Under 35 U.S.C. 154(b), the term of this patent shall be extended for 0 days.

(21) Appl. No.: 09/048,643

(22) Filed: Mar. 26, 1998

(51) Int. Cl.$^7$ ............................................... A61B 5/00
(52) U.S. Cl. ................................. 600/427; 600/523
(58) Field of Search ................................... 600/407, 510, 600/523, 373, 374, 509, 427; 382/128; 128/920, 922; 606/41; 607/122

(56) References Cited

U.S. PATENT DOCUMENTS

| | | | |
|---|---|---|---|
| 5,694,945 | * | 12/1997 | Ben-Haim . |
| 5,722,402 | * | 3/1998 | Swanson et al. . |
| 5,724,985 | * | 3/1998 | Snell et al. . |
| 5,840,031 | * | 11/1998 | Crowley . |
| 5,916,163 | * | 6/1999 | Panescu et al. . |
| 6,106,460 | * | 8/2000 | Panescu et al. . |
| 6,115,626 | * | 8/2000 | Whayne et al. . |

* cited by examiner

Primary Examiner—Marvin M. Lateef
Assistant Examiner—Shawna J Shaw
(74) Attorney, Agent, or Firm—Lyon & Lyon LLP

(57) ABSTRACT

An interface for association with an electrode structure deployed in contact with heart tissue generates a real image of the electrode structure acquired by an imaging device. The interface also generates an idealized image of the electrode structure based at least in part upon the real image. The interface displays either the real image, or the idealized image, or both on a display screen.

19 Claims, 32 Drawing Sheets

SYSTEMS AND METHODS FOR CONTROLLING THE USE OF DIAGNOSTIC OR THERAPEUTIC INSTRUMENTS IN INTERIOR BODY REGIONS USING REAL AND IDEALIZED IMAGES

BACKGROUND OF THE INVENTION

This invention relates generally to systems for diagnosing and treating medical conditions using instruments deployed within a living body.

FIELD OF THE INVENTION

Multiple electrode arrays are used to diagnose or treat a variety of medical conditions.

For example, physicians use arrays of multiple electrodes to examine the propagation of electrical impulses in heart tissue to locate aberrant conductive pathways. The techniques used to analyze these pathways, commonly called "mapping," identify regions in the heart tissue, called foci, which can be ablated to treat the arrhythmia. When used for this purpose, the multiple electrode arrays are typically located in electrical contact with either epicardial or endocardial tissue. The multiple electrodes are coupled to an external cardiac stimulator, which applies electrical pacing signals through one or more electrodes at given frequencies, durations, or amplitudes to myocardial tissue, a process called "pacing." The multiple electrodes on the array are also typically coupled to signal processing equipment, called "recorders," which display the morphologies of the electrocardiograms or electrograms recorded during pacing. Sometimes, another roving electrode is deployed in association with the multiple electrode array, to pace the heart at various endocardial locations, a technique called "pace mapping." When it is desired to ablate myocardial tissue, an electrode coupled to a source of, e.g., radio frequency energy is deployed.

In conducting these diagnostic or therapeutic procedures, the physician must compare all paced electrocardiograms or electrograms to those previously recorded during an induced arrhythmia episode. The physician also must know the position of all deployed electrodes in order to interpret the data in a meaningful way. The physician also needs to be able to accurately maneuver and position the roving or ablation electrode, when used. For these reasons, these procedures required a considerable degree of skill and experience on the part of the attending medical personnel.

Conventional systems and methods designed to aid the physician in his difficult task became impractical and unwieldy as new technology provides more sophisticated arrays, have more electrodes arranged with increased density. With larger and more dense electrode arrays, the number of possible failure modes also increases. Conventional systems and methods cannot automatically and continuously monitor the status of the more sophisticated arrays, to warn the physician in the event of an opened or shorted electrode condition or other malfunction.

Thus, there is a need for improved systems and methods for manipulating and monitoring the use of multiple electrode arrays, as well as systems and methods for processing, monitoring, and interpreting data from multiple electrode arrays in an efficient, organized manner.

SUMMARY OF THE INVENTION

According to the invention, systems and methods provide an interface for association with an electrode structure which, in use, is deployed in contact with heart tissue to perform a diagnostic or therapeutic procedure. The interface comprises a display screen, and an interface manager coupled to the display screen. The interface manager includes a first function to generate a real image of the electrode structure acquired by an imaging device. The interface manager includes a second function to generate an idealized image of the electrode structure based at least in part upon the real image. The interface manager includes a third function to display a view image comprising either the real image, or the idealized image, or both on the display screen.

Other features and advantages of the inventions are set forth in the following Description and Drawings, as well as in the appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. System Overview

Figure 1:
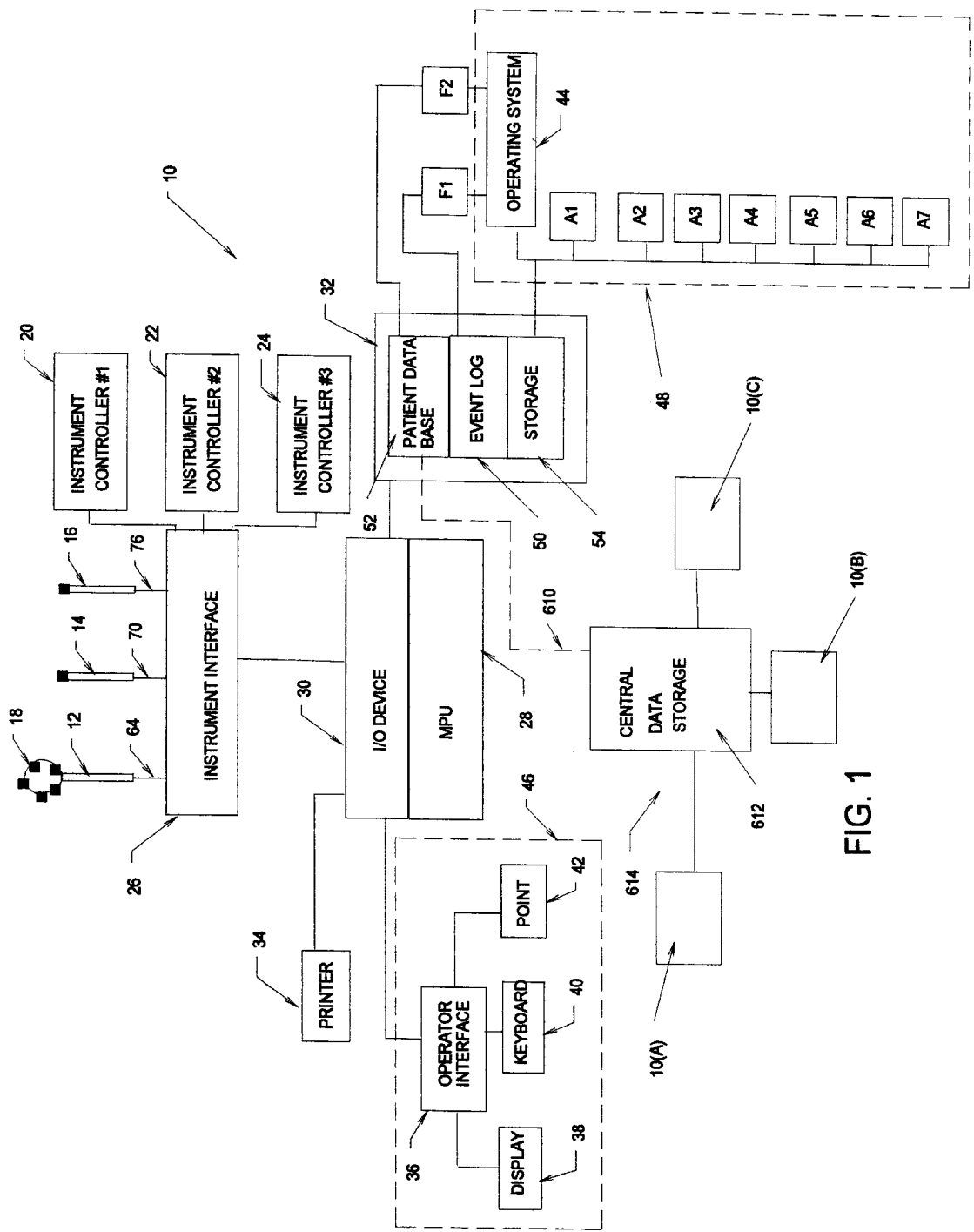
FIG. 1 is a schematic view of a system, which couples several individually controlled diagnostic or therapeutic instruments to a main processing unit through an instrument interface and which includes a graphical user interface (GUI)

FIG. 1 shows a system 10 for diagnosing, treating or otherwise administering health care to a patient.

The system 10 includes various diagnostic or therapeutic instruments. For the purpose of illustration, FIG. 1 shows three instruments 12, 14, and 16.

In the illustrated embodiment, the instrument 12 comprises an array of multiple electrodes 18. In the illustrated embodiment, the instruments 14 and 16 each comprises an operative element usable for some diagnostic or therapeutic purpose.

For example, one of the operative elements 14 or 16 can comprise a device for imaging body tissue, such as an ultrasound transducer or an array of ultrasound transducers, or an optic fiber element, or a CT or MRI scanner. Alternatively, one of the operative elements 14 or 16 can comprise a device to deliver a drug or therapeutic material to body tissue. Still alternatively, one of the operative elements 14 or 16 can comprise a device, e.g., an electrode, for sensing a physiological characteristic in tissue, such as electrical activity in heart tissue, or for transmitting energy to stimulate or ablate tissue.

When deployed in the body, the operative elements 14 and 16 can be readily moved relative to the multiple electrode array 12. For this reason, the instruments 14 and 16 will also each sometimes be called a "roving instrument."

The system 10 includes one or more instrument controllers (designated 20, 22, and 24). In use, the controllers 20, 22, and 24 condition an associated instrument 12, 14, and 16 to perform its desired diagnostic or therapeutic functions. The functions depend upon the medical objectives of the system 10. Representative specific examples will be described later.

To aid in coordinating signal and data flow among the controllers 20, 22, and 24 and their linked instruments, the system 10 includes an instrument manager or interface 26. The interface 26 couples the instrument controllers 20, 22, and 24 to their respective instruments 12, 14, and 16, establishing electrical flow paths, which process the various diagnostic or therapeutic data and signals in an organized and efficient fashion. Generally speaking, the interface 26 serves as a master switching unit, which governs the connections linking the instrument controllers 20, 22, and 24 to the individual instruments 12, 14, and 16.

The interface 26 can comprise an integrated module, or an assembly of discrete components. Further details of a representative embodiment for the interface 26 will described later.

The system 10 also includes a main processing unit (MPU) 28. In the illustrated embodiment, the MPU 28 comprises a Pentium™ type microprocessor, although other types of conventional microprocessors can be used.

The MPU 28 includes an input/output (I/O) device 30, which controls and monitors signal and data flow to and from the MPU 30. The I/O device 30 can comprise, e.g., one or more parallel port links and one or more conventional serial RS-232C port links or Ethernet™ communication links.

The I/O device 30 is coupled to a data storage module or hard drive 32, as well as to the instrument interface 26 and a printer 34.

The system 10 also includes an operator interface module 36, which is coupled to the I/O device 30. In the illustrated embodiment, the operator interface 36 includes a graphics display monitor 38, a keyboard input 40, and a pointing input device 42, such as a mouse or trackball. The graphics display monitor 38 can also provide for touch screen input.

The system 10 includes an operating system 44 for the MPU 28. In the illustrated embodiment, the operating system 44 resides as process software on the hard drive 32, which is down loaded to the MPU 28 during system initialization and startup. For example, the operating system 44 can comprise a Microsoft WINDOWS® 3.1, WINDOWS 95® or NT operating system. Alternatively, the operating system 44 can reside as process software in EPROM's in the MPU 28.

In the illustrated embodiment, the operating system 44 executes through the operator interface 36 a graphical user interface, or GUI 46, the details of which will be described later. Preferably, the GUI 46 is configured to operate on a WINDOWS® compatible laptop or desktop computer. The GUI 46 can be realized, e.g., as a "C" language program implemented using the MS WINDOWS™ application and the standard WINDOWS 32 API controls, e.g., as provided by the WINDOWS™ Development Kit, along with conventional graphics software disclosed in public literature.

The MPU 28, hard drive 32, and the components of the operator interface 36 can be implemented in a conventional lap top or desktop computer, which serves as a host for the operating system 44 and GUI 46. Other computer system forms can, of course, be used, e.g., using a server to host the operating system 44 and GUI 46 for a network of workstations, each of which comprises an operator interface 36.

In whatever form, the operating system 44 administers the activation of a library 48 of control applications, which are designated, for purpose of illustration, as A1 to A7 in FIG. 1. In the illustrated embodiment, the control applications A1 to A7 all reside in storage 54 as process software on the hard drive 32 and are down loaded and run based upon operator input through the GUI 46. Alternatively, all or some of the control applications A1 to A7 can reside as process software in EPROM's in the MPU 28, which can likewise be called and run through the GUI 46.

Each control application A1 to A7 prescribes procedures for carrying out given functional tasks using the system 10 in a predetermined way. Of course, the number and functions of the applications A1 to A7 can vary.

In the illustrated and preferred embodiment, the library 48 includes one or more clinical procedure applications, which are designated A1 and A2 in FIG. 1. Each procedure application A1 and A2 contains the steps to carry out a prescribed clinical procedure using the system 10. When run by the operating system 44, each procedure application A1 and A2 generates prescribed command signals, which the I/O device 30 distributes via the instrument interface 26 to condition the instrument controllers 20, 22, and 24 to perform a desired task using the instruments 12, 14, and 16. The I/O device 26 also receives data from the instrument controllers 20, 22, and 24 via the instrument interface 26 for processing by procedure application A1 or A2 being run. The GUI 46 presents to the operator, in a graphical format, various outputs generated by the procedure application A1 or A2 run by the operating system 44 and allows the user to alter or modify specified processing parameters in real time. Further details of specific representative procedure applications A1 and A2 will be described in greater detail later.

In the illustrated and preferred embodiment, the library 48 also includes one or more specialized navigation applications A3 and A4. The navigation applications A3 and A4, when run by the operating system 44, allow the operator to visualize on the GUI 46 the orientation of the multiple electrode array 12 and roving instruments 14 and 16 when deployed in an interior body region. The navigation applications A3 and A4 thereby assist the operator in manipulating and positioning these instruments to achieve the diagnostic or therapeutic results desired. In the illustrated embodiment, one navigation application A3 constructs an ideal or virtual image of the deployed array 12 and the roving instruments 14, and 16, while the other navigation application A4 displays an actual, real-time image of these instruments 12, 14, and 16. One or both of the navigation applications A3 and A4 can also display in graphical form on the GUI 44 information to aid the operator in interpreting data acquired by the multiple electrode array 12 and roving instruments 14 and 16 when deployed in an interior body region.

In the illustrated and preferred embodiment, the library 48 also includes one or more utility applications A5 to A7. The utility applications A5 to A7 carry out, e.g., system testing, system servicing, printing, and other system support functions affecting the all applications. Further details of representative utility applications A5 to A7 will be described in greater detail later.

The operating system 44 also includes one or more speciality functions (designated F1 and F2 in FIG. 1), which run in the background during execution of the various applications A1 to A7. For example, one function F1 can serve to establish and maintain an event log 50, stored in the hard drive 32, which keeps time track of specified important system events as they occur during the course of a procedure. Another function F2 can serve to enable the operator, using the GUI 44, to down load patient specific information generated by the various applications A1 to A7 to the hard drive 32 as data base items, for storage, processing, and retrieval, thereby making possible the establishment and maintenance of a patient data base 52 for the system 10.

As described, the system 10 is well adapted for use inside body lumens, chambers or cavities for either diagnostic or therapeutic purposes. For this reason, the system 10 will be described in the context of its use within a living body.

The system 10 particularly lends itself to catheter-based procedures, where access to the interior body region is obtained, for example, through the vascular system or alimentary canal. Nevertheless, the system 10 can also be used in association with systems and methods that are not necessarily catheter-based, e.g., laser delivery devices, atherectomy devices, transmyocardial revascularization (TMR), percutaneous myocardial revascularization (PMR), or hand held surgical tools.

For example, the system 10 can be used during the diagnosis and treatment of arrhythmia conditions within the heart, such as ventricular tachycardia or atrial fibrillation. The system 10 also can be used during the diagnosis or treatment of intravascular ailments, in association, for example, with angioplasty or atherectomy techniques. The system 10 also can be used during the diagnosis or treatment of ailments in the gastrointestinal tract, the prostrate, brain, gall bladder, uterus, and other regions of the body.

For the purpose of illustration, representative components of the system 10 will be described in the context of the diagnosis and treatment of abnormal cardiac conditions. In this environment, the multiple electrode array 12 and roving instruments 14 and 16 are deployable within or near a heart chamber, typically in one of the ventricles.

A. Operating Instruments

The structure of the array of multiple electrodes 18 carried by the first instrument 12 can vary. In the illustrated embodiment (see FIG. 2), the instrument 12 comprises a composite, three-dimensional basket structure 58 that is carried at the distal end of a catheter tube 56 for introduction into the targeted heart chamber. The basket structure includes eight spaced apart spline elements (alphabetically designated A to H in FIG. 2) assembled together by a distal hub 60 and a proximal base 62. Each spline A to H, in turn, carries eight electrodes 18, which are numerically designated on each spline from the most proximal to the most distal electrode as 1 to 8 in FIG. 2. The basket structure 58 thus supports a total of sixty-four electrodes 18, which FIG. 2 identifies alphanumerically by spline and electrode order, e.g., (A,8), which identifies the most distal electrode on spline A. Of course, a greater or lesser number of spline elements and/or electrodes 18 can be present.

Each spline element A to H preferably comprises a flexible body made from resilient, inert wire or plastic. Elastic memory material such as nickel titanium (commercially available as NITINOL™ material) can be used. Resilient injection molded plastic or stainless steel can also be used. Each spline element A to H is preferably preformed with a convex bias, creating a normally open three-dimensional basket structure.

The basket structure 58 is deployed in the heart by advancement through a conventional guide sheath (not shown) snaked through the vasculature. The guide sheath compresses and collapses the structure 58. Retraction of the guide sheath allows the structure 58 to spring open into the three-dimensional shape shown in FIG. 2. Further details of the structure and deployment of the multiple electrode structure can be found in U.S. Pat. No. 5,647,870, which is incorporated herein by reference.

Each of the electrodes 18 is electrically connected to an individual conductor in a multiple conductor cable 64 (see FIG. 1 also). The cable 64 terminates in one or more connectors, through which electrical connection can be made to the individual conductors and, hence, to the individual electrodes. The connectors are coupled to the instrument interface 26.

The instrument 12 need not be configured as a basket 58. For example, the array can take the form of an elongated electrode array, which can be straight, curved, or formed into a loop. For another example, a three-dimensional structure can be formed carrying dual outer and inner arrays of electrodes. Various other configurations for multiple electrode arrays are shown in copending U.S. patent application Ser. No. 08/938,721, filed Sep. 26, 1997, and entitled "Systems and Methods for Generating Images of Structures Deployed Within Interior Body Regions."

In the illustrated embodiment (see FIG. 2), the first roving instrument 14 is also carried at the distal end of a catheter tube 66 for deployment and manipulation in the body. In the illustrated embodiment representative for the system 10, the instrument 14 comprises an electrode 68 intended, in use, to sense electrical activity in heart tissue, as well as to transmit energy to stimulate or ablate tissue. The electrode 68 is electrically connected by a cable 70 to the instrument interface 26.

The second roving instrument 16 comprises an imaging device 72. The imaging device 72 operates using a selected visualizing technique, e.g., fluoroscopy, ultrasound, CT, or MRI, to create a real-time image of a body region. A cable 76 conveys signals from the imaging device 72 to the instrument interface 26.

B. Instrument Controllers

In the representative embodiment (see FIG. 2), the instrument controller 20 comprises at least one external cardiac stimulator. The cardiac stimulator 20 hosts a selection of diagnostic procedures, which generates electrical pulses of various duration, number, and cycles. The pulses stimulate or pace myocardial tissue, so that resultant electrical activity can be mapped.

A stimulator 20 of the type is of the type currently used in electrophysiology labs and can be commercially purchased, e.g., from Medtronic or Bloom, and. The system 10 can include additional stimulators, if desired. When multiple stimulators are present, the interface 26 can quickly switch between different pulse frequencies, durations, or amplitudes during pacing.

In the representative embodiment, the instrument controller 22 comprises an electrogram recorder of the type that is commercially available from, e.g., Prucka, Quinton, E for M, Bard, and Siemens. The electrogram recorder 22 functions to record, store, process, analyze, and display signals acquired by the electrodes on the basket structure 58 and as well as the roving electrode 68 during pacing.

In the representative embodiment, the instrument controller 24 comprises an appropriate controller for the imaging device 72. The controller 24 generates a video output from the signals generated by the device 72. The format of the video output can vary, e.g., it can comprise composite video, video-modulate RF signal, or RGB/RGBI including applicable TV standards (i.e. NTSC, PAL or SECAM).

Figure 2:
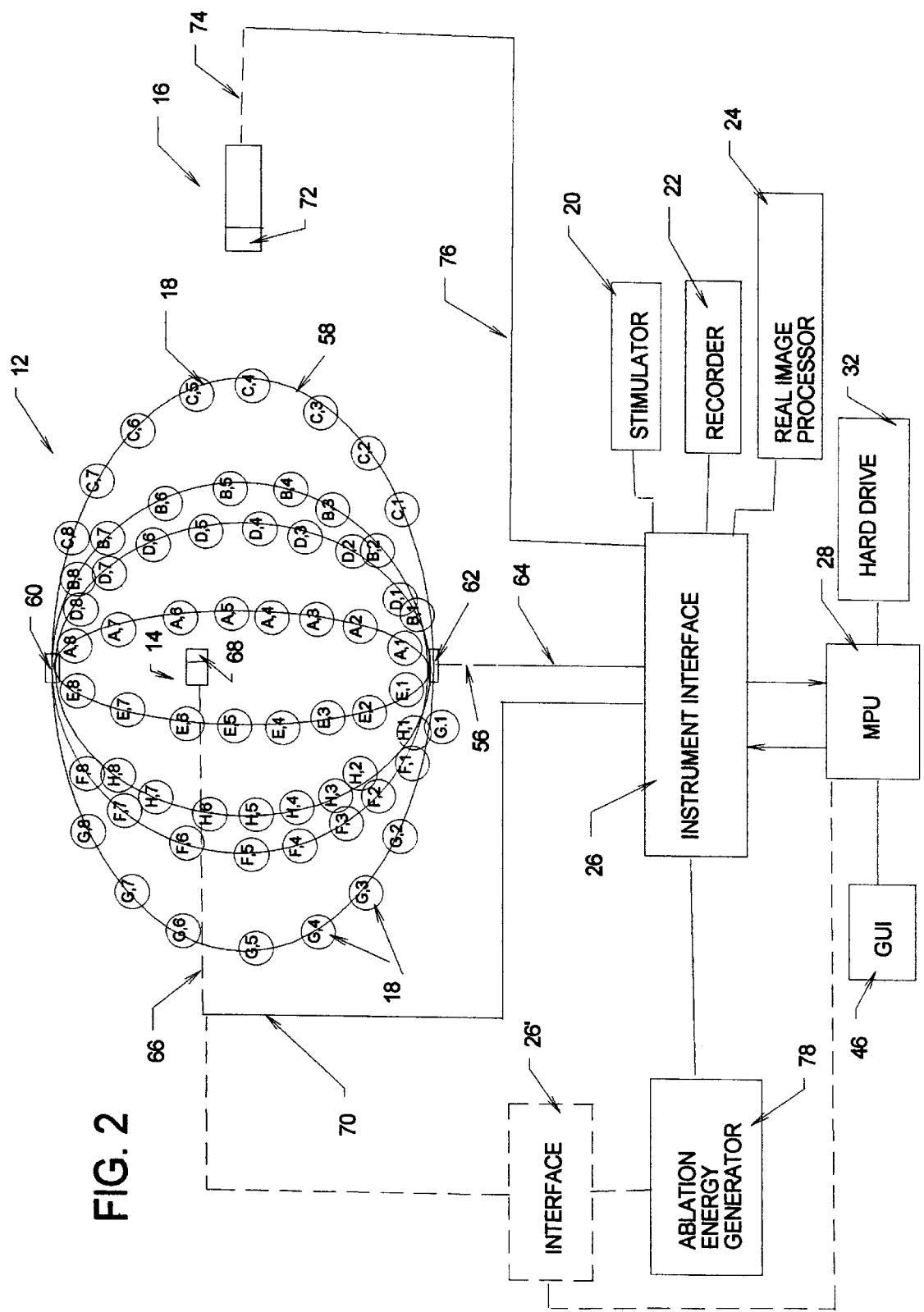
FIG. 2 is a schematic view of the representative instruments, including a multiple electrode basket, a roving electrode, and a roving imaging device, which are coupled to individual controllers via the instrument interface.

As shown in FIG. 2, a generator for transmitting radio frequency ablation energy can also be coupled to the roving electrode 68, through the instrument interface 26 (as shown in solid lines in FIG. 2), or through its own instrument interface 26' (shown in phantom lines in FIG. 2) coupled to the MPU 28.

C. The Instrument Interface

Figure 3:
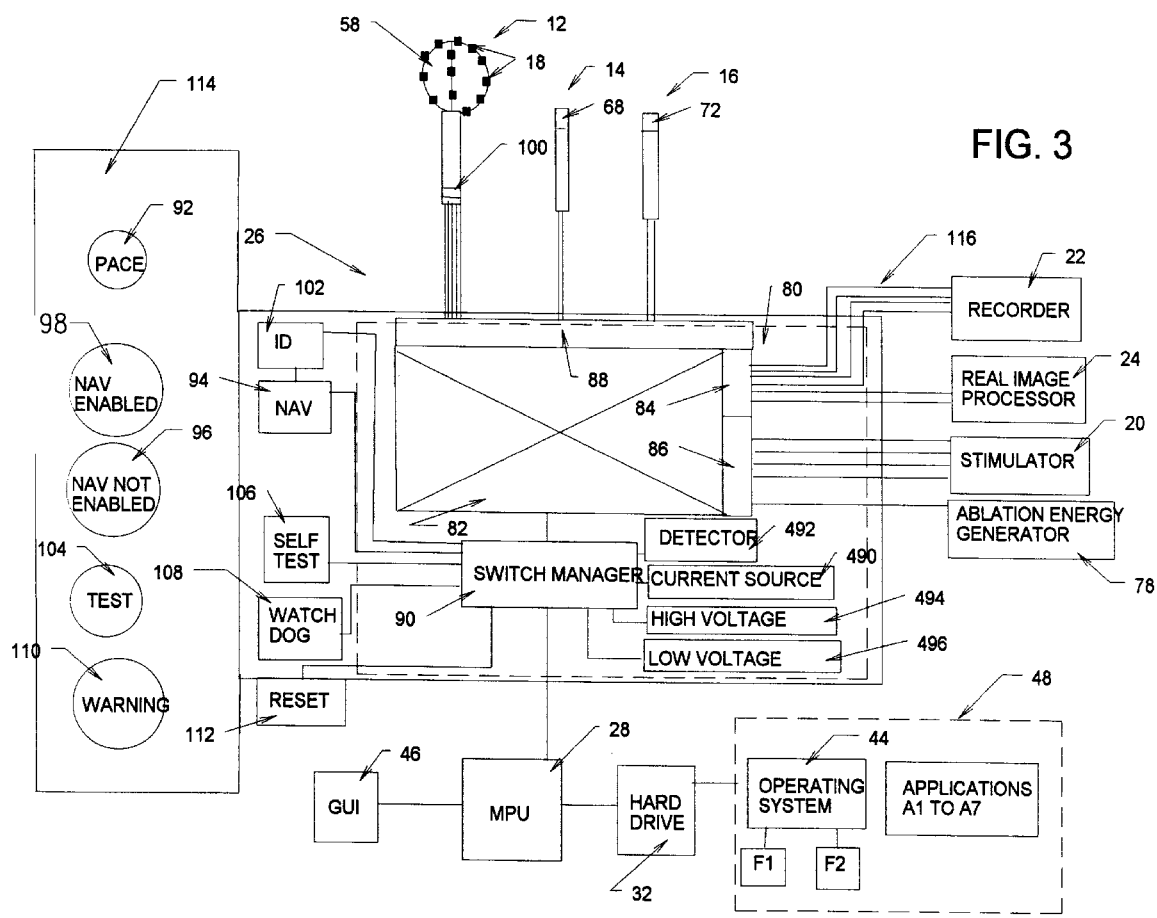
FIG. 3 is a schematic view of the instrument interface.

In the illustrated embodiment (see FIG. 3), the instrument interface 26 is centered around an application specific integrated circuit (ASIC) 80 of the type shown and described in U.S. application Ser. No. 08/770,971 entitled, "Unified Switching System for Electrophysiological Stimulation and Signal Recording and Analysis," filed Dec. 12, 1996, which is incorporated herein by reference. Alternatively, as previously stated, the interface 26 can comprise an assembly of separate components and not an integrated circuit.

In the illustrated embodiment, the ASIC 80 comprises a cross point switch matrix 82. The matrix 82 includes a block of primary analog input pins 84 through which low level external signals from the recorder 22 and real image processor 24 can be received. A block of additional analog input pins 86 are provided, through which high level external signals, such as those produced by the stimulator 20 or generator 78, can be received. The matrix 82 includes a block of analog output pins 88.

The matrix 82 enables any of the input pins 84/86 to be connected to any of the output pins 88. This operation permits, for example, various subsets of the electrodes 18 on the basket structure 58 to be connected to various subsets of input channels 116 of the electrogram recorder 22. In addition, any of the high level input pins 86 can be coupled to any of the primary input pins 84. This permits pacing pulses generated by the stimulator 20 to be applied through any of the electrodes 18 on the basket structure 58 or through the roving electrode 68. Alternatively, high level pacing pulse signals can be switched backward from any of the output pins 88 to any of the input pins 84, to permit "retrograde" pacing from the electrogram recorder 22, if it has pacing output capabilities. The various instruments 12, 14, and 16 are coupled to the ASIC 80 through appropriate isolation circuitry (not shown), which isolates the ASIC 80 from potentially damaging signals, currents and voltages.

The ASIC 80 includes embedded on-chip software that comprises a switch manager 90. In response from high level commands from the MPU 28 (which are generated by the selected application A1 to A7 or function F1 or F2 run by the operating system 44 on the MPU 28), the switch manager 90 configures the cross point switch matrix 82 to establish desired electrical connections among the various instruments 12, 14, and 16 and controllers 20, 22, and 24, to carry out various operating modes for the system 10.

The number and type of operating modes controlled by the switch manager 90 in large part parallel the number and type of applications A1 to A7 and functions F1 and F2 available for execution by the operating system 44.

For example, when the procedure applications A1 and A2 are executed, the switch manager 90 enters a procedure mode. In this mode, the manager 90 configures the multiple electrodes 18 on the basket structure 58 and the roving electrode 68 for recording or pacing based upon the command signals generated by the MPU 28.

The procedure mode carried out by the switch manager 90 is not necessarily constrained by the data channel limitations of the associated instrument controllers. For example, if the procedure application A1 or A2 calls for signal acquisition or pacing from sixty-four (64) electrodes, and the data acquisition capabilities of the electrogram recorder 22 happens to be only twenty-four (24) channels 116, the switch manager 90 configures the sixty-four (64) electrodes into four subsets of sixteen (16) electrodes, switching among the subsets to achieve the desired data acquisition task using the available channels 116 of the recorder 22. The interface 26 displays a visual PACE output, e.g., through a LED 92 on an exterior panel 114, which is activated when the stimulator 20 is coupled by the manager 90 to one or more instrument electrodes.

When the navigation application A3 or A4 is executed, the manager 90 is commanded by the MPU 28 to enable the navigation mode. During the navigation mode controlled by the virtual navigation application A3, the manager 90 periodically communicates to the MPU 28 the electrically sensed position of the roving electrode 68 for display in the GUI 46, using an embedded navigation routine 94, which will be described in greater detail later. In a preferred embodiment, the position reporting frequency is at least once per heart chamber cycle (i.e., once every 150 ms or greater).

When the navigation mode is controlled by real image application A4, the manager 90 inputs signals from the imaging device 72 to the processor 24, and outputs processed video signals to the MPU 28 for display on the GUI 46.

The interface displays visual NAVIGATION DISABLED and NAVIGATION ENABLED outputs, e.g., through LEDs 96 and 98 on the exterior panel 114. The NAVIGATION ENABLED LED 98 is activated when either navigation application A3 or A4 is executed and the navigation mode is enabled. Conversely, the NAVIGATION DISABLED LED 96 is activated when neither navigation application A3 or A4 are executed.

In an illustrated embodiment, the multiple electrode instrument 12 carries an electrical identification code 100, which uniquely identifies the physical property and configuration of the electrodes on the basket structure 58. The switch manager 90 includes an embedded ID routine 102, which electrically senses the code 100 and inputs configuration data according to the code 100 for use in the navigation routine 94. The code 100 can be variously implemented, e.g., in an integrated circuit, which expresses the code 100 in digital form, or as separate electrical elements, such as several resistors having different resistance values which express the digits of the code 100.

In the illustrated embodiment, application A5 constitutes a prescribed testing utility. When the testing application A5 is executed on the MPU 28, the switch manager 90 responds to high level commands generated by the application A4 to stop recording, pacing, and navigation switching tasks, and configure the cross point switch matrix 82 to perform various prescribed system tests, e.g., open or short-circuit detection and confirmation of system connections. More details of these and other utility applications A6 and A7 will be described later. The interface displays a visual TEST output, e.g., through a LED 104 on the exterior panel 114, which is activated when the testing application A5 is executed.

In a preferred embodiment, the embedded on-chip switch manager 90 also runs a self-test routine 106 immediately after power-on or hardware reset. In the self-test mode, the manager 90 verifies the overall functionality of the interface 26. The embedded on-chip switch manager 90 also continuously self-checks the interface's functionality, e.g., through a conventional watchdog routine 108, which interrupts improper software execution. When a failure is detected (or when the self-test mode fails), the manager 90 switches to a safe mode, where command execution is inhibited and the navigation mode is disabled. The interface 26 displays a visual WARNING output, e.g., through a LED 110 on the exterior panel 114, which is activated when the safe mode is entered. The interface remains in the safe mode until the user presses a reset button 112 on the exterior of the interface 26 to continue.

D. The Operator Interface and GUI

In the illustrated embodiment, the graphics display device 38 of the operator interface 36 supports SVGA or comparable display of graphic information by the GUI 46. The MPU 28 preferable has a SPECfp92 benchmark of at least 25 to support rapid update of graphical information on the GUI 46.

1. Start-Up

Figure 4:
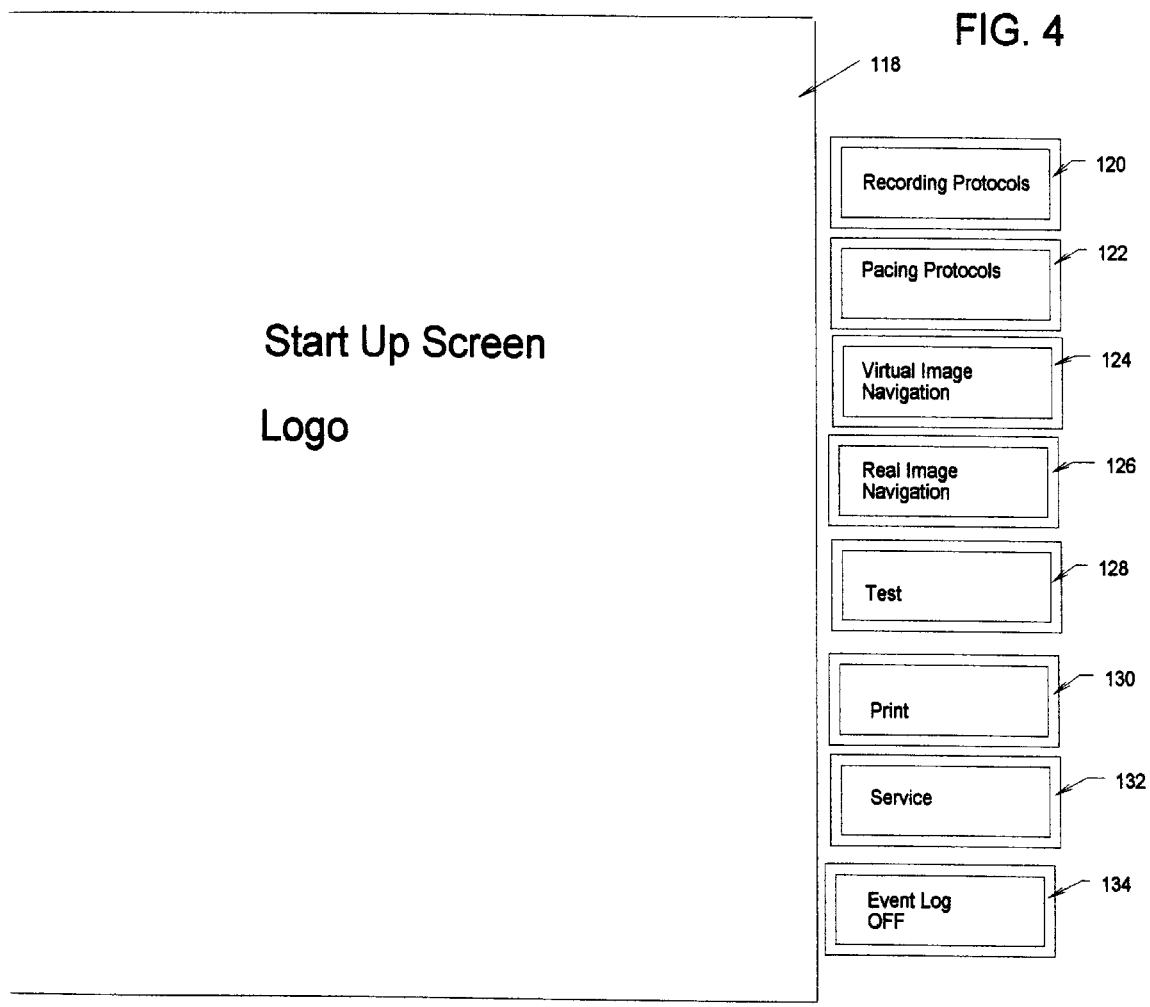
FIG. 4 is a depiction of the start-up screen of the GUI.

Upon boot-up of the MPU 28, the operating system 44 implements the GUI 46. The GUI 46 displays an appropriate start-up logo and title image, followed by the START-UP screen 118, as shown in FIG. 4.

The START-UP screen 118 includes a column of icon push button controls 120 to 134, which are labeled for each of the main operating modes or functions available to the MPU 28 for execution.

The illustrated embodiment provides these executable modes: RECORDING PROTOCOLS (executing Application A1); PACING PROTOCOLS (executing Application A2); VIRTUAL IMAGE NAVIGATION (executing Application A3); REAL IMAGE NAVIGATION (executing Application A4); TEST (executing Application A5); PRINT (executing Application A6); and SERVICE (executing Application A7). Selected a button control 120 to 134 using the pointing device 42 or keyboard 40 (or touching the screen itself, if a touch screen feature is provided), causes the operating system 44 to down load and implement the associated application on the MPU 28.

In the illustrated embodiment, the additional icon push button control 134 labeled EVENT LOG is present on the start up scree 118. This control 134, when selected, toggles on and off the display of an event log, which the Event Log Function F1 of the operating system 44 continuously executes in the background. The Event Log Function F1 records specified major events that occur during the course of a given procedure. More details about the Event Log Function F1 and the EVENT LOG toggle button 134 will be provided later.

As will be demonstrated later, each of these push button controls 120 to 134 are displayed by the GUI 46 throughout a given operating session, regardless of what application is being executed. The push buttons 120 and 132 for the executable modes are displayed in one color (e.g., grey) when not selected and a different color (e.g., green) when selected. The label of the toggle push button 134 changes when selected.

In the illustrated embodiment, the operating system 44 itself is not available for general use by the operator, outside of the confines of the GUI 46. Access to the operating system 44 is restricted only to authorized service personnel, through executing the password protected SERVICE application A7, which will be described later.

Further details of the GUI 46 will be now described by selecting and executing the applications A1 to A7, as well as describing the execution of the functions F1 and F2.

2. Recording Protocols Application (A1)

The selection of the RECORDING PROTOCOLS push button 120 executes the recording protocols application (A1). The recording protocols application A1 operates to define or configure electrode subgroups among the available electrodes 18 of the basket 58 and roving electrode 68, to feed myocardial signal data from the subgroups to the input channels 116 of the recorder 22.

Figure 5:
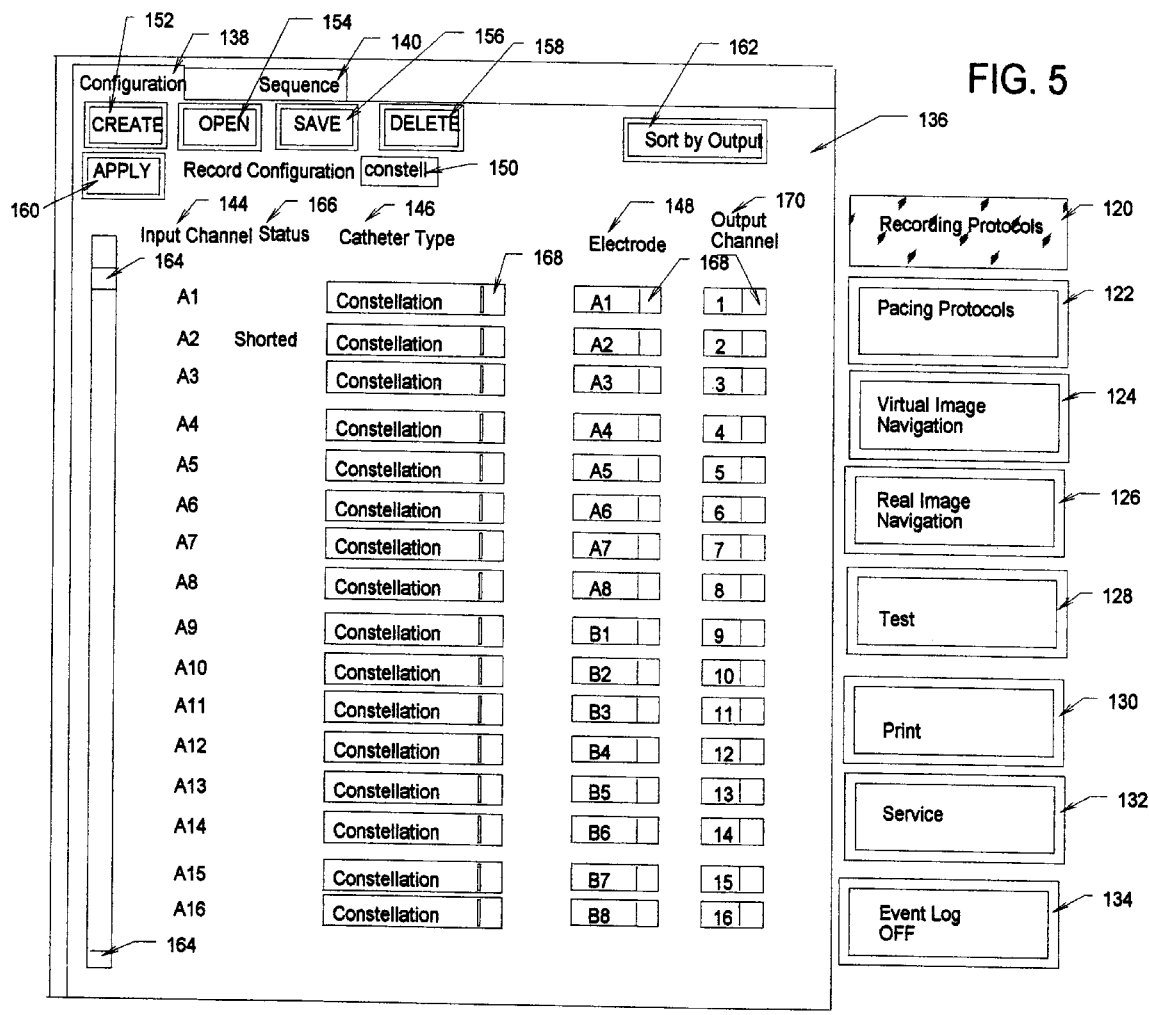
FIG. 5 is a depiction of the record protocols-configuration screen of the GUI.

The recording protocols application A1, when executed by the MPU 28, displays a first sub-window 136, as shown in FIG. 5. As can be seen in FIG. 5, all main mode and function push buttons 120 to 134 remain displayed on the right side of the window 136. The selected push button 120 changes color when selected, while the other non-selected push buttons 122 to 134 remain displayed in their original state.

Figure 6:
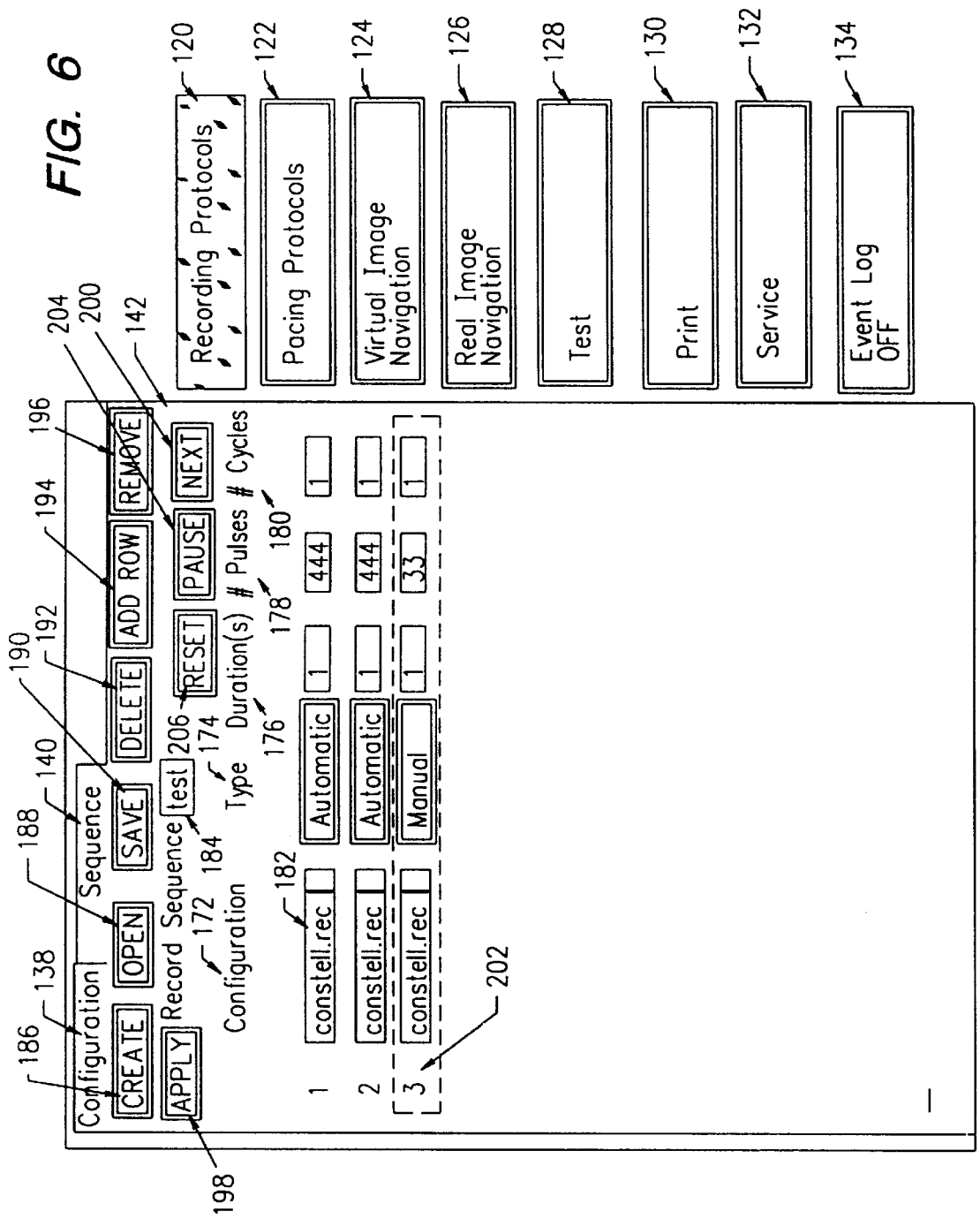
FIG. 6 is a depiction of the record protocols-sequence screen of the GUI.

The first sub-window 136 allow the operator to define a Recording Configuration and a Recording Sequence. By selected the CONFIGURATION control tab 138 or the SEQUENCE control tab 140, the operator is able to switch between the recording configuration window 136 (shown in FIG. 5) and a recording sequence window 142 (shown in FIG. 6).

a. Recording Configuration

The recording configuration window 136 displays an INPUT CHANNEL column field 144, a CATHETER TYPE column field 146, and an ELECTRODE column field 148. Information in these fields 144, 146, and 148 together define a currently valid Catheter Configuration, which is assigned by default or by the operator an identifier in a RECORD CONFIGURATION field 150. The recording configuration window 136 also displays an OUTPUT CHANNEL field 170, which assigns an output channel number to each electrode, which also becomes a component of the valid Catheter Configuration 150.

A catheter configuration can be saved as a file on the hard drive, for processing, editing, and retrieval. Various file management push button controls (CREATE 152, OPEN 154, SAVE 156, DELETE 158, and APPLY 160) are provided for this purpose.

The INPUT CHANNEL field 144 identifies the input channels 116 of the recorder 22. The OUTPUT CHANNEL field 170 identifies the output channel assigned to each electrode. By default, the rows are indexed by INPUT CHANNEL in numeric or alpha-numeric order. Alternatively, the operator can index in channel output order, by selecting the SORT BY OUTPUT control button 162. When selected, the SORT BY OUTPUT control button label toggles to SORT BY INPUT. The operator can always select indexing the display either between recorder input channel or electrode output channel.

The operator can scroll using the control buttons 164, up and down the INPUT CHANNEL field 144 in conventional fashion. In the illustrated embodiment, the scrolling occurs in steps of sixteen, and information is updated across all fields 144, 146, and 148 while scrolling.

For each INPUT CHANNEL, the recording protocols application A1 accepts a STATUS field input 166, which indicates an non-operational state of the channel (e.g., shorted or open). No input in the STATUS field 166 (i.e., a blank field) indicates a good operational channel. The STATUS field 166 receives input from the test application A5, or from self-tests conducted by the switch manager 90, as already described.

The INPUT CHANNEL field 144 can be edited by the operator, to associate available electrodes 18 or 68 with available recorder input channels 116, as desired. As earlier explained, the operator can configure the INPUT CHANNELS into electrode subgroups, so a recorder 22 having a lesser number of input channels than the number of electrodes can nevertheless be used to record and process signals obtained by the multiple electrode basket 58. For example, to configure sixty-four (64) electrode channels for input using a thirty-two (32) channel recorder, electrodes A1 to D8 define the first electrode subgroup, and E1 to H8 define the next electrode group.

The OUTPUT CHANNEL field 170 can likewise be edited using a drop down menu control 168 or by input from the keyboard 40. The OUTPUT CHANNEL field 170 accepts a numeric value from between 1 to 72.

The CATHETER TYPE field 146 contains an key word identifier, which indicates the type of instrument carrying the electrodes 18 or 68, e.g., whether it is a multiple electrode basket structure 58 (which is designated "Constellation" in FIG. 5, which in shorthand identifies a CONSTELLATIONS Catheter sold by EP Technologies, Inc.), or a roving electrode 68 (for example, in shorthand, "Roving"), or some other type of identifiable electrode configuration or shape typically used by electrophysiologists (for example, in shorthand, "HIS, CS, HRA, RVA," etc.).

The CATHETER TYPE column field 146 is editable, either by predefined default drop down menu control 168 or by input from the keyboard 40. Thereby, the operator can, in a single record configuration, associate with the recorder input channels, several different types of electrode-carrying instruments, e.g., a multiple electrode basket 58 and a roving electrode 68, and others.

The ELECTRODE field 148 identifies each electrode 18 on the instrument by the assigned numeric, alphabetic, or alpha-numeric code. As already explained, for the basket 58, the electrodes 18 are identified A1, B4, C6, etc., with the splines alphabetically identified (A, B, C, D, etc.), and the electrodes on each spline numerically identified from the distal to the proximal end of the spline (1, 2, 3, etc.). Instruments with a single electrode or linear or curvilinear arrays of electrodes, like the roving electrode 58, can numerically identify electrodes in order from distal to proximal end of the instrument. The ELECTRODE column field 148 is editable, either by predefined default drop down menu controls 168 or by input from the keyboard 40.

Selecting the file management control buttons (CREATE 152, OPEN 154, SAVE 156, DELETE 158), the operator can, respectively, establish a new record configuration, retrieve an existing record configuration as a file from the hard drive 32, save a new or edited record as a file to the hard drive 32, or delete a record file from the hard drive 32. By selecting the APPLY control button 160, the operator commands the instrument interface 26 to be configured according to the current recording configuration.

b. Record Sequence

The record sequence window 142 (see FIG. 6) is displayed by selecting the Sequence tab 140. The window 142 lists the recording sequences and the order in which they are applied to the recorder 22 via the instrument interface 26. The window 142 displays a CONFIGURATION column field 172, a SEQUENCE TYPE column field 174, a DURA- TION column field 176, a #PULSES column field 178, and a #CYCLES column field 180. Each row of information in these fields 174 to 180 together define a recording protocol. The numeric order in which the protocols are listed comprises a recording sequence. In the illustrated embodiment, the window 142 allows for a maximum of fourteen rows, that is, fourteen different recording protocols for each recording sequence.

Each recording protocol (row) in a given recording sequence is assigned a file name 182, either by default or by the operator for storage in the hard drive, with a ".rec" file identifier. The hard drive 32 can carry pre-determined recording protocols as .rec files, so that the operator need not be concerned about inputting the specifics of the recording sequence. The file name 182 appears in the CONFIGURATION field 172. The recording sequence, which lists the order of the protocols, is also assigned a file name 184 for storage in the hard drive 32, either by default or by the operator. This file name 184 appears in the editable Record Sequence field.

Various file management push button controls (CREATE 186, OPEN 188, SAVE 190, DELETE 192, ADD ROW 194, REMOVE 196, and APPLY 198) are provided for establishing, retrieving, saving, removing, or otherwise editing recording files retaining the protocols and recording sequences configurations.

The SEQUENCE TYPE field 174 constitutes a control button, which toggles between Automatic mode and Manual mode. When set to Automatic mode, the recording application A1 applies the protocol row to the interface box without requiring operator intervention, following the timing specified either in the DURATION field 176 or #PULSES field 178, as will be described later. When set to Manual mode, the recording application A1 requires operator intervention before applying the protocol. In the illustrated embodiment, the operator intervenes by selecting the NEXT control button 200 in the sequence window 142.

The DURATION field 176, the #PULSES field 178, and the #CYCLES field 180 are each editable by input from the keyboard 40. The number inserted by the operator in the DURATION field 176 specifies the number of seconds for which the specified protocol is to be applied to the instrument interface 26. The number inserted by the operator in the #PULSES field 178 specifies the number of pacing pulses for which the specified protocol is to be applied to the instrument interface 26. The longer of the time period specified in the DURATION field 176 and #PULSES field 178 controls the timing of the protocol applied to the instrument interface 26. The number inserted by the operator in the #CYCLES field 180 specifies the number of cycles for which either the duration field value or pacing pulse field value controls the application of the protocol to the instrument interface 26.

By selecting the file management control buttons (CREATE 186, OPEN 188, SAVE 190, DELETE 192), the operator can, respectively, establish a new record configuration, retrieve an existing record as a file from the hard drive 32, save a new or edited record as a file to the hard drive 32, or delete a record file from the hard drive 32.

By selecting the ADD ROW control button 194, the operator adds a new row of editable fields, in which the operator can add a new recording protocol for the recording sequence, which is assigned the next sequential row number. Conversely, by selecting the REMOVE control bottom 196, the operator can remove any highlighted protocol row.

By selecting the APPLY control button 198, the recording application A1 commands the instrument interface 26 to be configured to carry out the recording sequence specified in the record sequence window 142. The recording application A1 starts applying the sequencing row by row to the instrument interface 26 in row order. The recording application A1 displays a highlight 202 around the sequence row that is being currently applied to the instrument interface 26.

By selecting the PAUSE control button 204, the recording application A1 interrupts the sequencing. The control button label toggles to RESUME, which permits, when selected, the resumption of the sequencing, toggling the label back to PAUSE.

By selecting the RESET control button 206, the recording application A1 begins sequencing at the first listed row, regardless of the current status of the sequence. The RESET control button 206 is active for selection only when the sequencing is paused or otherwise not being applied. Furthermore, changes to any editable field in the window 142 are accepted only when the sequencing is paused or not being applied.

3. Pacing Protocols Application (A2)

The selection of the PACING PROTOCOLS push button 122 executes the recording protocols application A2. The pacing protocols application A2 operates to define or configure the connectivity among the one or more pacing stimulators 20 and the electrodes connected via the instrument interface 26.

Figure 7:
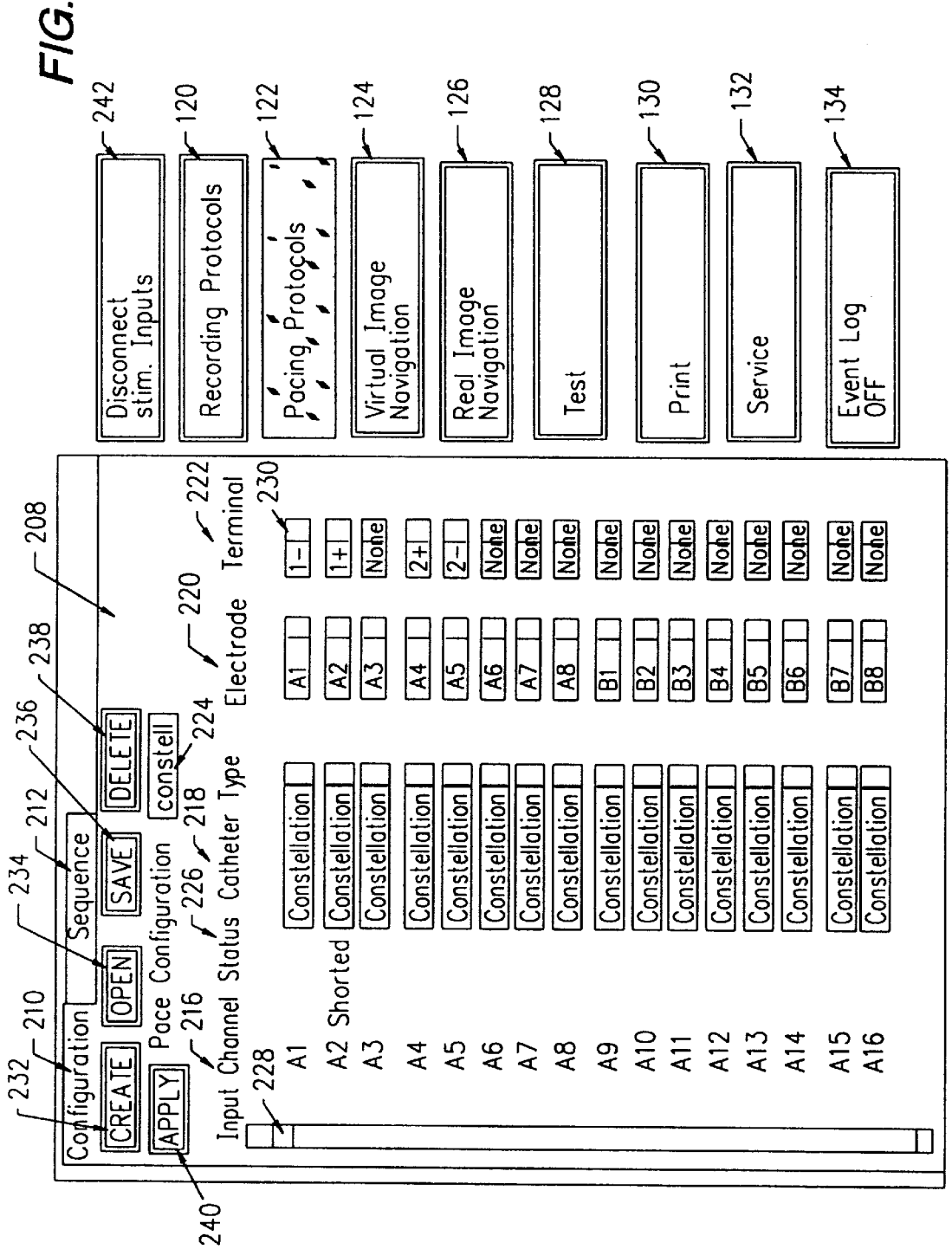
FIG. 7 is a depiction of the pace protocols-configuration screen of the GUI.

The pacing protocols application A2, when executed by the MPU 28, displays a first sub-window 208, as shown in FIG. 7. As can be seen in FIG. 7, the main mode or function push buttons 120 to 134 still remain in view on the right side of the window 208 in their original first color, except the selected push button control 122, which changes color when selected.

The first sub-window 208 allow the operator to define a Pacing Configuration and a Pacing Sequence. By selected the CONFIGURATION control tab 210 or the SEQUENCE control tab 212, the operator is able to switch between the pacing configuration window 208 (shown in FIG. 7) and a pacing sequence window 214 (shown in FIG. 8). This GUI architecture parallels that of the recording application (A1), just described.

a. Pacing Configuration

The configuration window 208 displays an INPUT CHANNEL column field 216, a TERMINAL TYPE column field 218, an ELECTRODE column field 220, and a TERMINAL column field 222.

The information contained in the INPUT CHANNEL field 216, the TERMINAL TYPE field 218, and the ELECTRODE field 220 corresponds to the information inputted by the operator on the current recording configuration window 136 (FIG. 5) in the INPUT CHANNEL field 144, CATHETER TYPE field 146, and ELECTRODE field 148, respectively. The recording configuration name in current recording configuration window 136 (FIG. 5) (i.e., "constell") also appears in the PACE CONFIGURATION field 224 of the pacing configuration window 208. The pacing application A2 does not allow the operator to edit these fields 216, 218, and 220 in the pacing configuration window 208, thereby maintaining conformity between the current recording configuration and the current pacing configuration. For each INPUT CHANNEL 216, the pacing protocols application also displays a STATUS field input 226, which corresponds with the information in the STATUS field 166 in the current recording configuration window 136 (FIG. 5). The operator can scroll using the control buttons 228, up and down the rows in known fashion, which, in the illustrated embodiment, is in steps of sixteen. Information across all fields is updated during scrolling.

The only editable field in the pacing configuration window 208 is the TERMINAL column field 222. The editable TERMINAL field 222 allows for selection of known electrode terminals by a drop down menu control 230. The drop down menu 230 contains the selections: "None", "1", "1+", "2–", and "2+". The pacing application A2 replaces a previously entered value of the TERMINAL field 222 in a different row with "None" whenever the operator selects the same terminal value in another row from the drop down menu 230.

Selecting the file management control buttons SAVE 236 or DELETE 238, the operator can save a new or edited record as a file to the hard drive 32, or delete a record file from the hard drive 32. The CREATE 232 and OPEN 234 control buttons are not active on the pacing configuration sheet, as a pacing configuration can be established or retrieved only in conjunction with the establishment or retrieval of a recording configuration, through the recording applications A1.

By selecting the APPLY control button 240, the operator commands the instrument interface 26 to be configured according to the current pacing configuration. When the APPLY button 240 has been selected, a DISCONNECT STIMULATOR control button 242 appears in the window 208, preferably in red or another distinguishing color. The DISCONNECT STIMULATOR button 242 allows the operator to immediately interrupt transmission of the pacing inputs to the hardware interface 26. The DISCONNECT STIMULATOR control button 242, once implemented, continues to be displayed throughout the remainder of the operating session, regardless of what application is implemented, unless selected to interrupt pacing.

b. Pacing sequence

Figure 8:
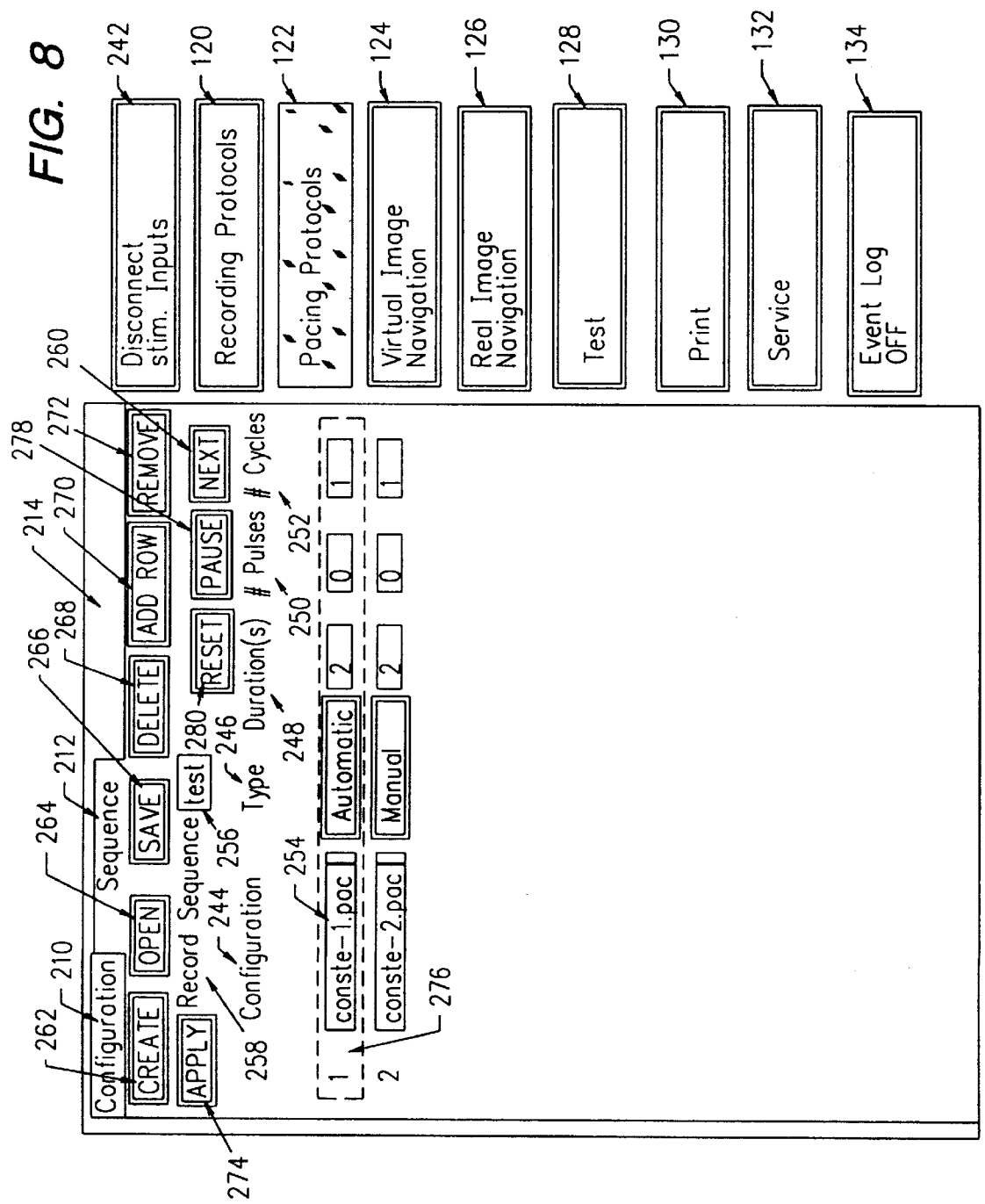
FIG. 8 is a depiction of the pace protocols-sequence screen of the GUI.

Selection of the Sequence tab 212 in the configuration window 208 opens the pacing sequence window 214 shown in FIG. 8. The pacing sequence window 214 lists the pacing protocols and the order in which they are applied to the stimulator 20 via the instrument interface 26.

The window 214 displays a CONFIGURATION column field 244, a SEQUENCE TYPE field column 246, a DURATION column field 248, a #PULSES column field 250, and a #CYCLES column field 252. Each row of information in these fields 244 to 252 together define a pacing protocol. The numeric order in which the protocols are listed comprises a pacing sequence. In the illustrated embodiment, the window 214 allows for a maximum of fourteen rows, that is, fourteen different pacing protocols for each pacing sequence.

Each pacing protocol (row) in a given pacing sequence is assigned a file name 254, either by default or by the operator for storage in the hard drive 32, with a ".pac" file identifier. The hard drive 32 can carry pre-determined pacing protocols as .pac files, so that the operator need not be concern about inputting the specifics of the pacing sequence. The file name 254 appears in the CONFIGURATION field 244. The pacing sequence, listing the order of the protocols, is also assigned a file name 256 for storage in the hard drive 32, which is the same name assigned to the current recording sequence (i.e. "test"), which appears in the Pacing Sequence field 258.

The SEQUENCE TYPE field 246 constitutes a control button, which toggles between Automatic mode and Manual mode. When set to Automatic mode, the pacing application A2 applies the protocol row to the instrument interface 26 without requiring operator intervention, following the timing specified either in the DURATION field 248 or #PULSES field 250, as will be described later. When set to Manual mode, the pacing application requires operator intervention before applying the protocol. In the illustrated embodiment, the operator intervenes by selecting the NEXT control button 260 in the sequence window 214.

The DURATION field 248, the #PULSES field 250, and the #CYCLES field 252 are each editable by keyboard entry. The number inserted by the operator in the DURATION field 248 specifies the number of seconds for which the specified protocol is to be applied to the interface 26. The number inserted by the operator in the #PULSES field 250 specifies the number of pacing pulses for which the specified protocol is to be applied to the interface 26. The longer of the time period specified in the DURATION field 248 and #PULSES field 250 controls the timing of the protocol applied to the interface 26. The number inserted by the operator in the #CYCLES field 252 specifies the number of cycles for which either the duration field value or pacing pulse field value controls the application of the protocol to the interface 26.

Selecting the file management control buttons (CREATE 262, OPEN 264, SAVE 266, DELETE 268), the operator can, respectively, establish a new record configuration, retrieve an existing record as a file from the hard drive 32, save a new or edited record as a file to the hard drive 32, or delete a record file from the hard drive 32. By selecting the ADD ROW control button 270, the operator adds a new row of editable fields, in which the operator can add a new recording protocol of the recording sequence, which is assigned the next sequential row number. By selecting the REMOVE control button 272, the operator can remove any highlighted protocol row.

By selecting the APPLY control button 274, the pacing application A2 commands the instrument interface 26 to be configured to carry out the pacing sequence specified in the pacing sequence window 214. The pacing application A2 starts applying the sequencing row by row to the instrument interface 26 in the order specified. The pacing application A2 applies a highlight 276 about the sequence row in the window 214 that is being currently applied to the instrument interface 26.

When the APPLY button 274 has been selected, the DISCONNECT STIMULATOR control button 242 appears, preferably in red or another distinguishing color, to allow the operator to immediately interrupt transmission of the pacing inputs to the instrument interface. As before described, the DISCONNECT STIMULATOR control button 242, once implemented, continues to be displayed throughout the remainder of the operating session, regardless of what application is implemented, unless selected.

By selecting the PAUSE control button 278, the pacing application A2 temporarily interrupts the pacing sequence. The control button label toggles to RESUME, which permits, when selected, the resumption of the sequencing, toggling the label back to PAUSE.

By selecting the RESET control button 280, the recording application begins sequencing at the first listed row, regardless of the current pacing status. The RESET control button 280 is active for selection only when the sequencing is paused or not otherwise being applied. Furthermore, changes to any editable field on the sheet is accepted only when the sequencing is paused or not being applied.

4. Virtual Image Navigation Application (A3)

Figure 9:
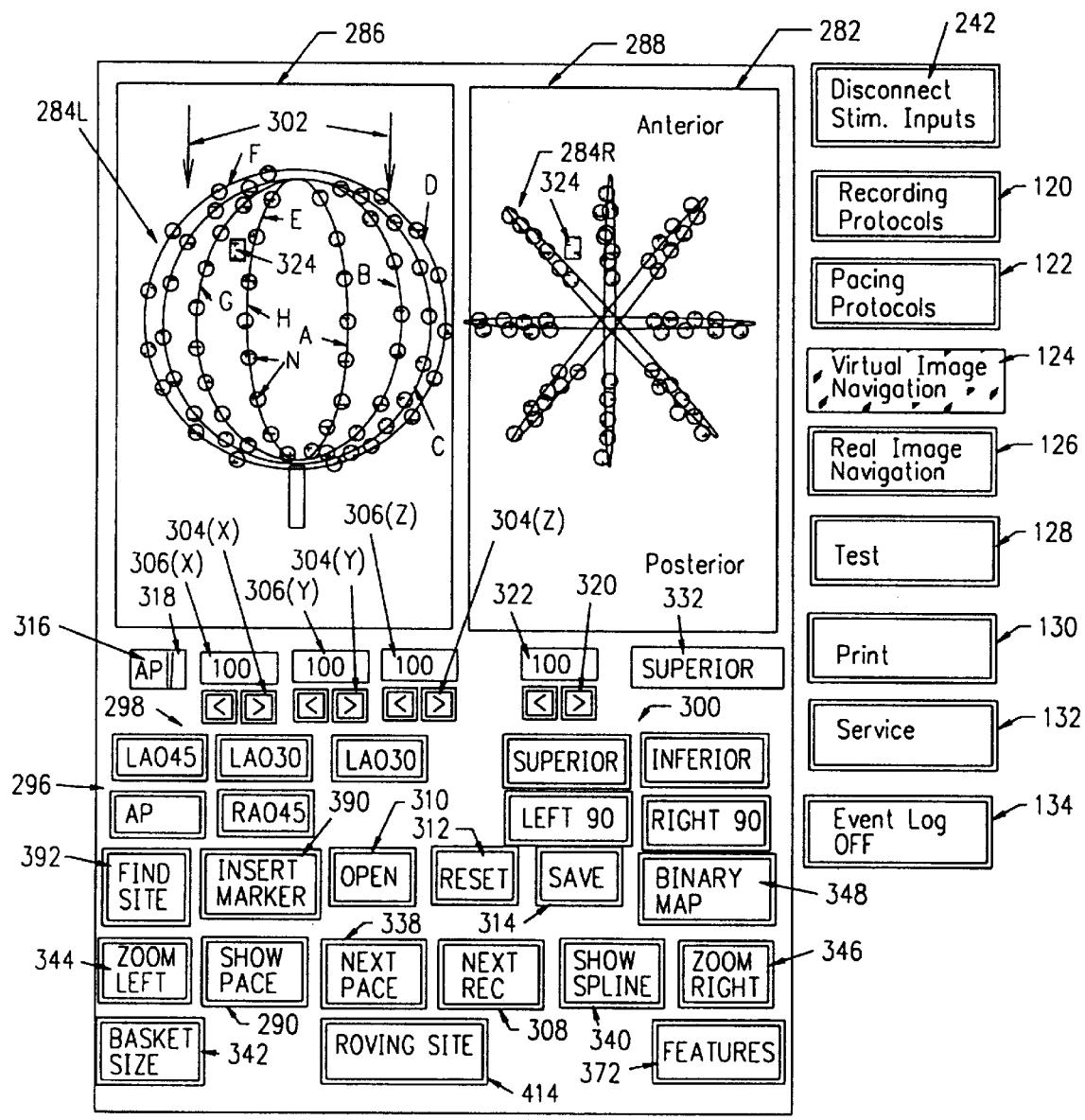
FIG. 9 is a depiction of the virtual image navigation screen of the GUI.

The selection of the VIRTUAL IMAGE NAVIGATION push button control 124 runs the virtual navigation application A3. The navigation application A3, when executed by the MPU 28, displays a virtual navigation window 282, as shown in FIG. 9. As can be seen in FIG. 9, the main application control push buttons 120 to 134 still remain in view on the right side of the navigation window 282 in their original first color, except the selected VIRTUAL IMAGE NAVIGATION push button control 124, which changes color when selected.

a. Basket Display

The virtual image navigation application A3 generates in the window 282 an idealized graphical image 284, which models the geometry of the particular multiple electrode instrument 12 deployed in the body region. In the illustrated embodiment, the instrument 12 is the three-dimensional basket 58, shown in FIG. 2, and the image 284 reflects this geometry modeled as a wire-frame image. By reference to this model image 284, the physician is able to visualize the location of each electrode and spline on the basket 58, as well as view the location of the roving electrode 68 relative to the basket image 284.

In the illustrated and preferred embodiment, the navigation application A3 provides split screen images (designated 284L and 284R) in a left panel 286 and a right panel 288.

To facilitate the creation of the images 284L and 284R, the electrical identification code 100 of the basket 58, previously described, also identifies the geometry and layout of electrodes on the basket 58. The navigation application A3 calls upon a library of idealized graphical images in hard drive storage 54, which reflect the different geometries identified by the code 100. Based upon the code 100, the navigation application A3 generates an idealized graphical image that corresponds to the geometry of the particular one in use. Alternatively, the toolbar 296 can include a Basket Size push button 342, which, when selected, opens a dialog box from which the operator can select one basket size from a listing of basket sizes.

In the illustrated embodiment (in which the array is a three dimensional basket 58), the model wire-frame image displays splines A to H in a selected first color, except for spline A, which is preferably displayed in a different color for reference and orientation purpose. By selecting the toggle Show Splines control button 340, the left and right images 284L and 284R display alphabetical spline labels A through H. The control button 340 toggles between Show Splines and Hide Splines, which removes the alphabetic labels.

In the left view, the X-axis of the image 284L is aligned by default along the major head-to-foot axis of the patient, the Y-axis is aligned along the shoulder-to-shoulder axis of the patient, and the Z-axis is aligned along the front to-back axis of the patient. The color of the splines A to H is preferably displayed in different hues or shades to indicate their three-dimensional orientation along the Z-axis of this coordinate system, e.g., a bright shade when the spline appears in the foreground (when the Z value>0) and a dark shade when the spline appears in the background (when the Z value<0). The idealized electrodes N can be represented by small rectangles or nodes.

Figure 10:
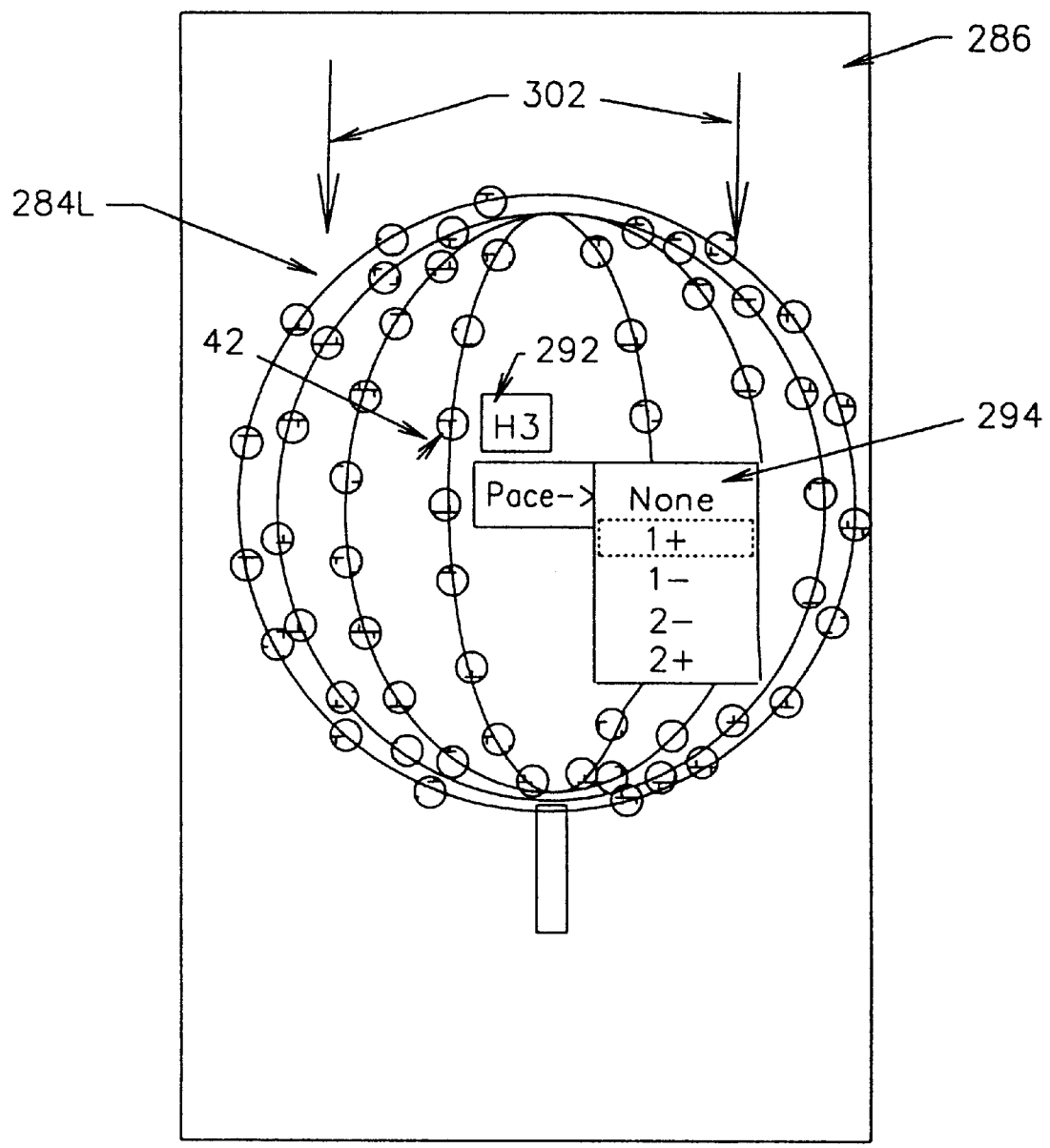
FIG. 10 is an enlarged view of the idealized image of the multiple electrode basket displayed by the virtual image navigation screen of the GUI.

In the illustrated embodiment (see FIG. 10), whenever the operator places the pointing device 42 over a given electrode N, a pop-up window 292 displays the location of a selected electrode N by spline electrode designation (A1, B2, etc., as explained above). When a pace sequence has been applied, the pop-up window 292 displays a menu 294, which highlights the pacing terminal type of the electrode (1+, 1−, 2+, 2−). If the pointing device 42 selects the roving electrode 68, the pop-up window 292 will identify it as "Roving."

As FIG. 9 shows, the left and right panels 286 and 288 make it possible to simultaneously display the images 284L and 284R from different idealized orientations. The navigation application A3 generates an Operational Screen Toolbar 296, which provides the physician with a variety of options to customize the idealized image 284L and 294R in each panel 286 and 288. Using the Toolbar 296, or by entering associated short-cut command entries using the keyboard 40, the physician is able to set up the desired images 284L and 284R in the left and right panels 286 and 288.

In the illustrated embodiment (see FIG. 9), the Toolbar 296 includes an array of Left View Control Buttons 298 for the image 284L displayed in the left panel 286. The left panel 286 shows the image 284L from preset right or left anterior angles or preset right or left posterior oblique angles. The Left View Control Buttons 298 allow the physician to choose among the preset orientations for the left image 284L, such as Left 45° or 30° (labeled respectively LAO45 and LAO30 in FIG. 9), Right 45° or 30° (labeled respectively RAO45 and RAO30 in FIG. 9), or Anterior/Posterior (labeled AP in FIG. 9). An Edit Control field 316 displays the currently selected preset orientation.

The Toolbar 296 also includes three sets of Orientation Control Buttons 304(X), 304(Y), and 304(Z) to customize the viewing angle for the left image 284L. The buttons 304 (X,Y,Z), when selected, cause the left image 284L to rotate about an idealized coordinate system located at center of the image 284L. Selection of the button 304 (X) rotates the image 284L in either a left-to-right or right-to-left direction. Selection of the button 304(Y) rotates the image 284L in either a top-to-bottom or bottom-to-top direction. Selection of the button 304(Z) rotates the image in either a clockwise or counterclockwise direction. Alternatively, or in combination with the Orientation Control buttons 304 (X,Y,Z) the navigation application A3 can provide for rotation of the left image 284L by conventional "dragging" of the pointing device 42.

The Orientation Angles for the present left image 284L are displayed in the fields 306 (X), 306 (Y), and 306(Z), respectively, on the Toolbar 296. The Toolbar 296 includes a RESET 312 button, which, when selected, inputs predefined default values as Orientation Angles in the fields 306(X), 306(Y), and 306(Z), and the left image 284L is redrawn accordingly.

The Edit Control field 316 includes a control button 318, which activates a drop down menu. The drop down menu lists the prescribed preset orientations (LAO45, LAO30, RAO45, RAO30, and AP) for selection. The drop down menu also permits the physician to include on the listing a title identifying a custom orientation set up using the Orientation Control buttons 304 (X,Y,Z). The physician is thereby able to set up and use custom orientations, along with the preset orientations.

The image 284R displayed in the right panel 288 is displayed from a selected orthogonal side angle relative to the left image 284L. The orientation of the right image 284R is adjusted to reflect the adjustments in the orientation of the left image 284L. An array of Right View Control Buttons 300 allows the physician to select among preset orthogonal views for the right image 284R, e.g., as labeled in FIG. 9, Superior, Inferior, Left 90, and Right 90. The preset Superior view is offset relative to the left image 284L 90 degrees about the Y-axis and 180 about the X-axis. The preset Inferior view is offset relative to the left image 284L minus 90 degrees about the Y-axis. The preset Left 90 view is offset relative to the left image 284L 90 degrees about the X-axis. The preset Right 90 view is offset relative to the left image 284L minus 90 degrees about the X-axis. A field 332 displays the name (e.g., Superior) of the selected preset view of the right image 284R.

In the illustrated embodiment, the navigation application A3 displays orientation arrows 302 in the left panel 286 to assist the operator in establishing the relationship between the left and right panel images 284L and 284R. The orientation arrows 302 point at the left image 284L along the horizontal or vertical axis of the line of sight along which the right image 284R is viewed for display in the right panel 288. As FIG. 9 also shows, the right panel 288 is also labeled Anterior (front) and Posterior (rear) to further help the physician orient the right image 284R. Other graphical clues, such as a bitmap human figure or small coordinate axes may be displayed to aid orientation.

In addition, the Toolbar 296 includes Fluor Angle Control buttons 320 and associated Fluoro Angle field 322. When selected, the buttons 320 rotate both the current left and right images 284L and 284R about the X-axis. The Fluoro Angle field 322 changes accordingly from zero to plus or minus 90 degrees. The buttons 320 allow the physician to match the orientation of the virtual images 284L and 284R with the orientation of a real image of the basket 58 provided by the imaging device 72. More details of this aspect of the system will be described later.

The Zoom Left push button 344 and the Zoom Right push button 346, when selected, allow the operator to call up a full-screen image of, respectively, the left image 284L or the right image 284R. All functions of the toolbar 296 remain function for the selected zoom image.

b. Binary Map Displays

In the illustrated embodiment, the Toolbar 296 (see FIG. 9) includes control buttons, which integrate for viewing in the display panels 286 and 288 functions performed by the record protocols application A1 and the pacing protocols application A2, previously described.

The SHOW PACE push button 290, when selected, opens in the right panel 286 a modified version of the Pacing Configuration window 208 (shown in full form in FIG. 7). The modified version displayed upon selection of the SHOW PACE button 290 includes the Pace Configuration field 224, the scroll bar 228, the Input Channel Field 216, the Terminal field 222, along with the SAVE 236, DELETE 238, and APPLY 240 control buttons.

The NEXT REC push button 308 on the Toolbar 296 has the same function as the Next control button 200 on the Record Sequence window 142 (see FIG. 6), by advancing the record sequence to the next row when the current row is designated Manual in the Type field 174 of the Record Sequence window 142. Similarly, the NEXT PACE push button 338 on the Toolbar 296 has the same function as the Next control button 260 on the Pace Sequence window 214 (see FIG. 8), by advancing the pace sequence to the next row when the current row is designated Manual in the Type field 246 of the Pace Sequence window 214.

Figure 11:
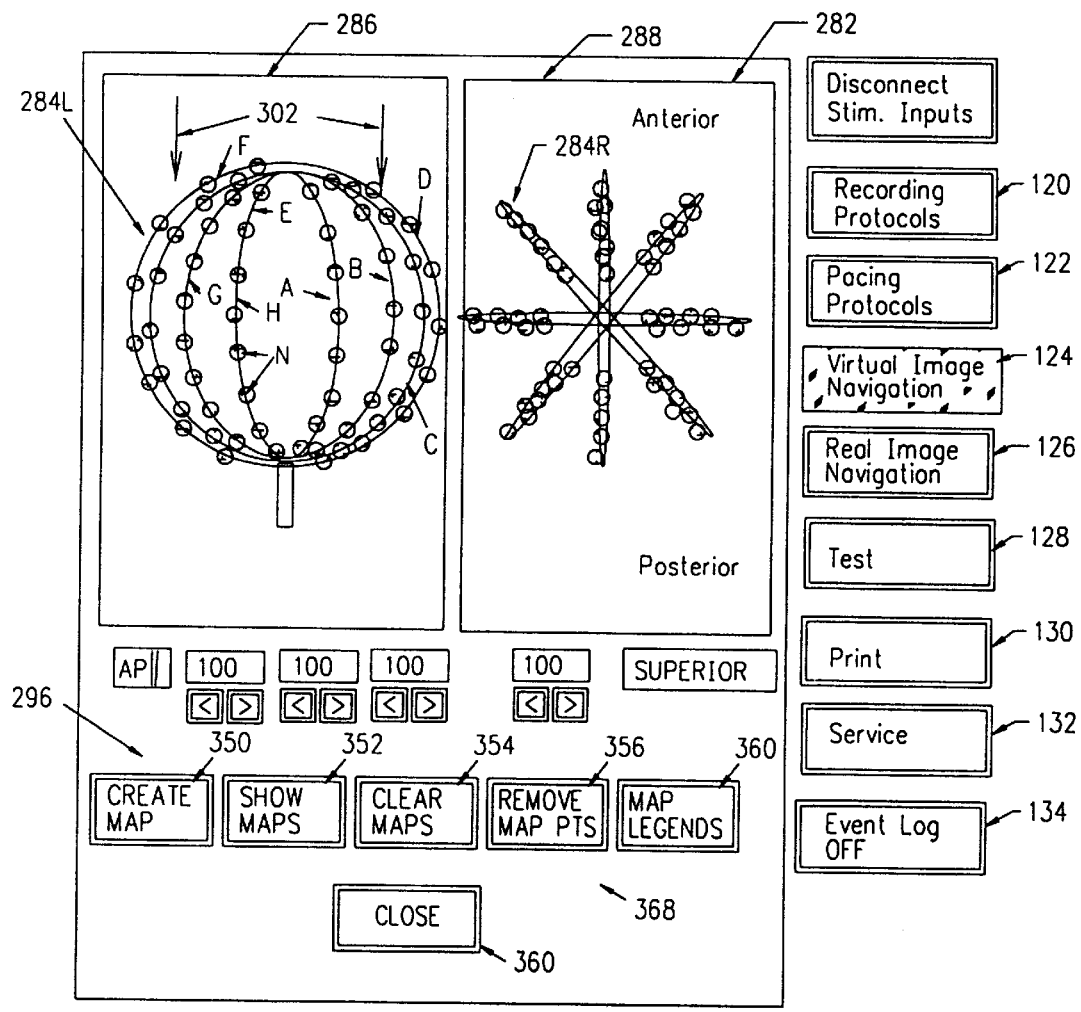
FIG. 11 is a depiction of the virtual image navigation screen of the GUI, with the Binary Map dialog box displayed.

The toolbar 296 also includes a Binary Map push button 348. When selected (see FIG. 11), the Binary Map push button 348 opens a push button selection menu 368 on the toolbar 296, listing CREATE MAP 350, SHOW MAPS 352, CLEAR MAPS 354, REMOVE MAP PTS 356, CLOSE 358, and MAP LEGENDS 360.

Selection of the CREATE MAP button 350, in turn, opens a sub menu 362 on the toolbar 296, which lists the default selections for the binary maps, along with a CLOSE button 370. In the illustrated embodiment, the sub menu 362 lists as map selections early activation, fractionation, good pace map, concealed entrainment, and user defined. When one of the listed choices is selected, the application A3 executes the desired mapping function based upon input from the record and pace applications A1 and A2.

Figure 12:
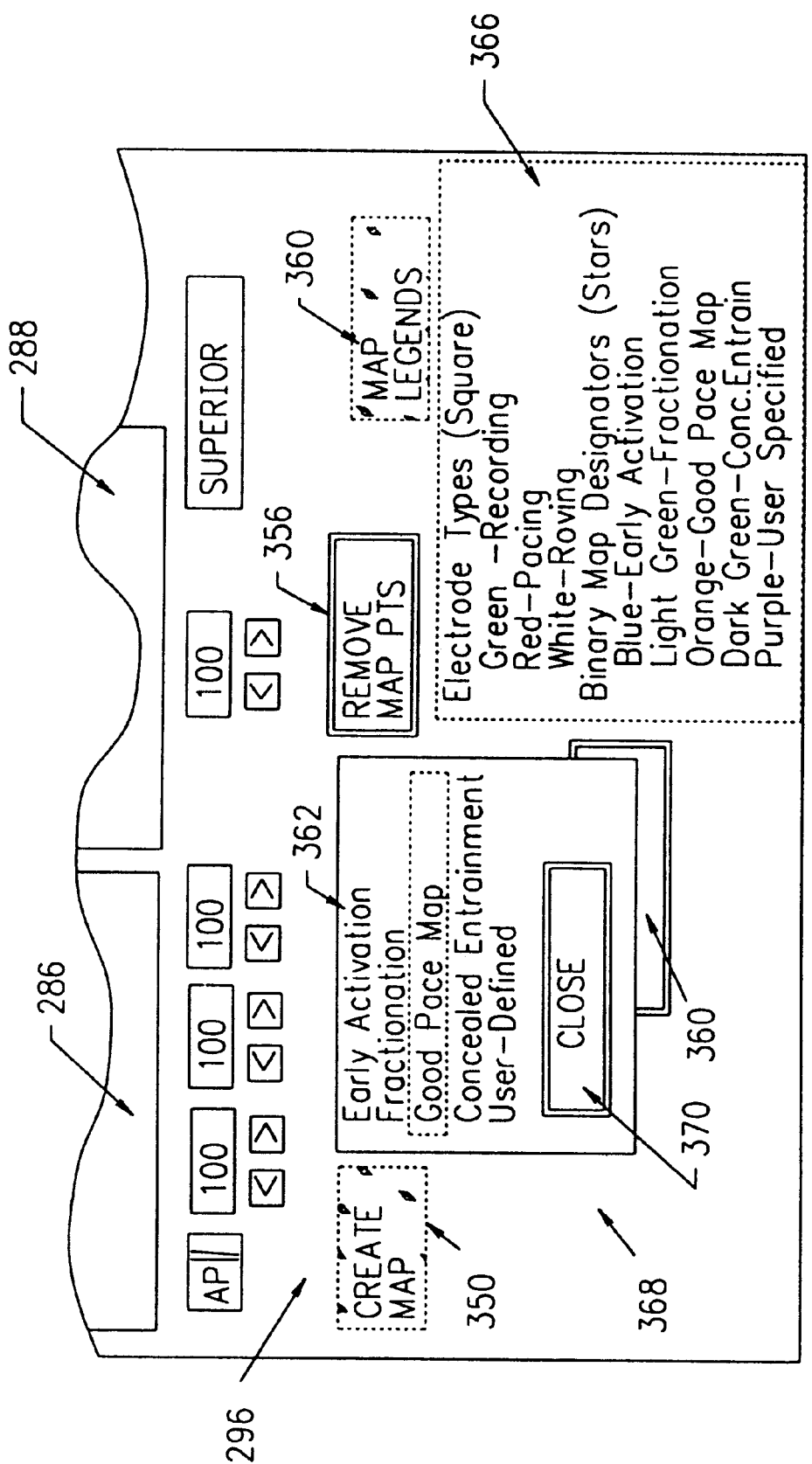
FIG. 12 is a depiction of the binary map dialog box with the Create Map control button selected.

To facilitate interpretation of the selected binary map, the application A3 annotates the images 284L and 284R with graphical symbols, called Binary Map Designators 364. The Designators identify by shaped and colored symbols the recording electrodes, the pacing electrodes, the roving electrode 68, and regions of electrical activity that the selected map function seeks out. Selecting the MAP LEGENDS button 360 (see FIG. 12) opens a sub menu 366, which lists the Binary Map Designators 364 by type, shape, and color. Using the pointing device 42, the operator is able to select among the individual electrodes on the displayed images 284L and 284R, to designate (e.g., by clicking) which electrode is to serve as a pacing electrode or as a recording electrode. The operator is thereby able to control the pacing and recording activities using the images 284L and 284R on the display panels 286 and 288.

The type of electrical activity highlighted by the Designators depends upon the type of binary map selected. For example:

The early activation map identifies and marks with the appropriate Binary Map Designator the electrodes where early depolarization of the heart tissue has occurred (early depolarization is often an indicator of abnormal heart tissue adjacent the electrode).

The fractionation map identifies and marks with the appropriate Binary Map Designator the electrodes where the electrograms sensed by such electrodes appear fractionated or broken in appearance (again, the existence of fractionated electrograms a particular electrode site is often an indicator of abnormal cardiac tissue at that site).

The good pace map identifies and marks with the appropriate Binary Map Designator the electrodes with a high pace mapping matching index. This index reflects how many of the morphologies of 12-lead surface electrocardiograms (ECG) acquired during non-induced arrhythmia match the morphologies of the same signals acquired during paced induced arrhythmia from the particular electrode. If by pacing from a particular electrode, a high number of the 12-lead ECG morphologies are similar during non-induced and pace-induced arrhythmia then it is likely that the particular electrode 18 resides close to an arrhythmogenic focus.

The concealed entrainment map identifies and marks with the appropriate Binary Map Designator the electrodes where arrhythmia entrainment was achieved (abnormal cardiac tissue often is located electrodes exhibiting concealed entrainment).

The user defined map function enables the operator to place a operator-specified Binary Map Designator on the displayed image 284L or 284R. The operator may position the graphical symbol by pointing and clicking the pointing device 42 on the selected electrode or spline region displayed on an image 284L or 284R. The operator can thus locate areas of cardiac tissue exhibiting certain preselected characteristics.

By selecting the SHOW MAPS button 352, the application A3 opens a dialog box listing all existing binary maps that have been created. Using the pointing device 42, the operator can quickly select and switch among any existing binary map. The ability to chose among different mapping functions are of importance in identifying potential ablation sites. Frequently, abnormal cardiac tissue, which can be effectively treated through ablation, often exhibits more than one abnormal characteristic. Such sites frequently appear on two or more of the early activation, fractionation and concealed entrainment maps. If the same electrode or groups of electrodes appear on two or more of the early activation, fractionation, good pace map and concealed entrainment maps, a likely site for ablation is particularly well indicated.

By selecting a Binary Map Designator 364 on one of the images 284L or 284R, and then selecting the REMOVE MAP PTS button 356 on the selection menu 368 (see FIG. 11), the operator deletes the selected Designator 364. By selecting the CLOSE button 370 on the selection sub menu 362, the application A3 dismisses the selection menu 362, deselects all Designators 364, and returns control to the main menu 368.

Selecting the CLEAR MAPS button 354 deletes and clear all existing binary maps. Selecting the CLOSE button 358 dismisses the section menu 368 and returns control to the navigation window 282 (shown in FIG. 9).

c. Anatomic Features Displays

Figure 13:
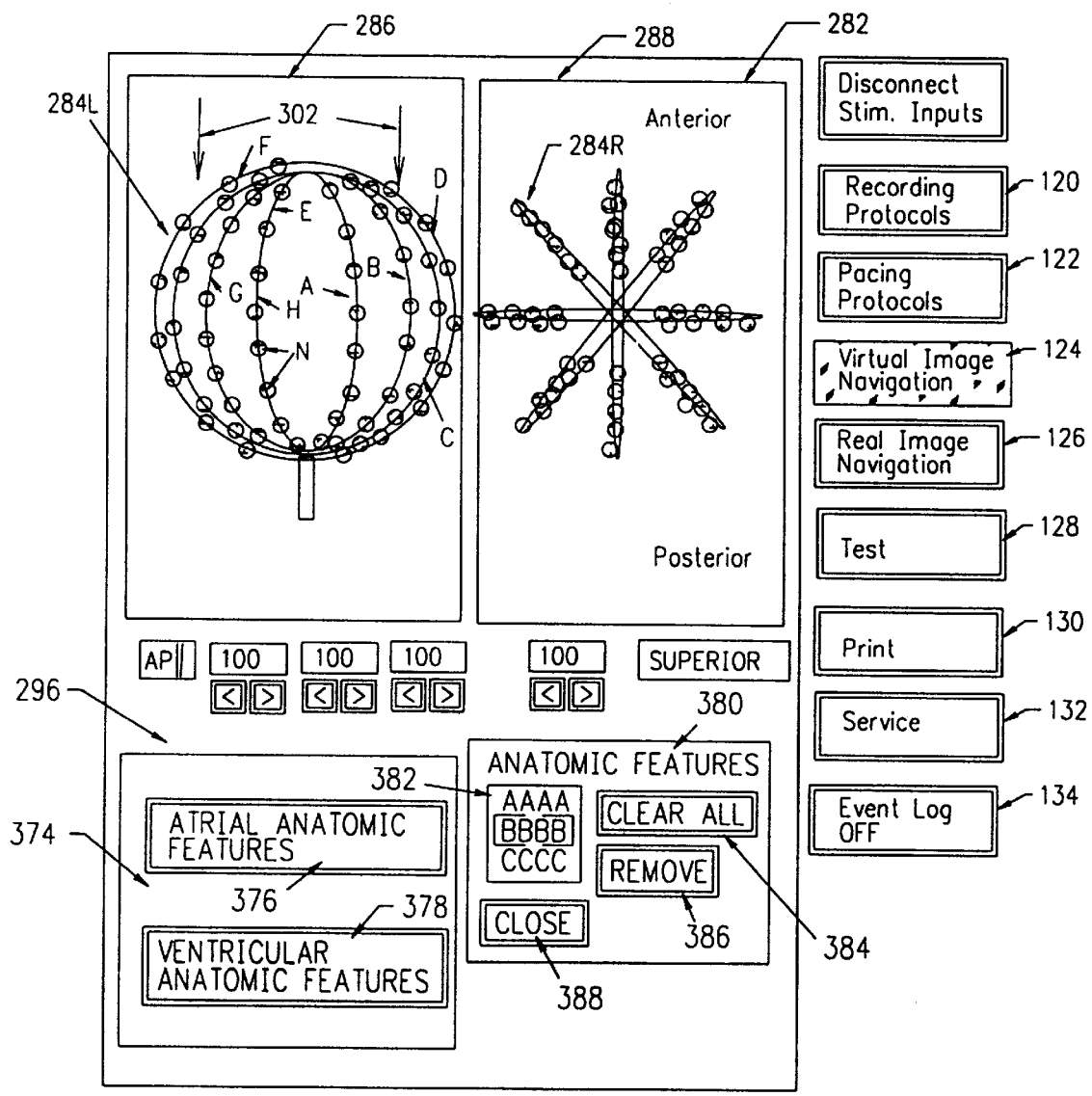
FIG. 13 is a depiction of the virtual image navigation screen of the GUI, with the Anatomic Features dialog boxes displayed.

The toolbar 296 also includes a Features push button 372. When selected (see FIG. 13), the Features push button 372 opens a push button selection menu 374, with buttons for selecting Atrial Anatomic Features 376 or Ventricular Anatomic Features 378. Selection of the button 376 or 378 opens a dialog box 380 for the selected region. The selection box 380 includes an anatomic features field 382 (listing e.g., the aortic valve, the inferior vena cava, the superior vena cava, etc.), along with control buttons labeled CLEAR ALL 384, REMOVE 386, and CLOSE 388. The application A3 maintains an editable text file, from which the features 382 in the field 382 are inputted.

Using the pointing device 42, the operator selects a feature from the field .382, drags the selected feature to an image 284L or 284R, and drops the selected feature at the appropriate location on the image 284L or 284R. Having the relative locations of such anatomical structures displayed relative to the images 284L and 284R helps the physician in guiding the roving electrode 68, and in mapping and treating the target myocardial tissue. The anatomic markers can be deleted as a group by clicking on the CLEAR ALL button 384, or can be selectively deleted by clicking the REMOVE button 386. Selection of the CLOSE button 388 dismisses the features selection boxes 374 and 380 and returns control to the navigation window 282 (shown in FIG. 9).

5. Image File Management

The navigation application A3 makes possible the establishment and processing of images files by providing Management Control Buttons, labeled OPEN 310 and SAVE 314, on the Toolbar 296 (see FIG. 9).

By selecting the SAVE button 314, the left image 284L, as currently configured in the left panel 286, is saved as an image file on the hard drive 32. Preferably, the image file is also saved as a record in the patient data base 52, the details of which will be described later.

When the SAVE button 314 is selected, the navigation application A3 reads the current values in the Orientation Angle fields 306(X), 306(Y), and 306(Z) (which can comprise a custom orientation) and computes the data necessary to recreate the saved orientation and the other prescribed preset orientations (LAO45, LAO30, RAO45, RAO30, and AP) for the left image 284L. Before saving, the navigation application A3 displays a dialog box asking the physician to designate which one of the preset or custom views constitutes the primary selected view.

The OPEN control button 310 allows the physician to retrieve an existing image record as a file from the hard drive 32 for further viewing and editing.

The navigation application A3 allows the physician to uniquely associate the image 284L/R with a file record, so that the physician can quickly recall, process, edit, or switch among any previously saved image.

a. Navigation Data

The navigation application A3 also displays in the left and right panels 286 and 288 an idealized image 324 of the roving electrode 68, showing its location relative to the idealized images 284L and 284R. For example, the roving electrode image 324 can appear as a square, with consideration for a Z-axis shadowing effect, as previously described for the splines. Byselectionn of the toggle ROVING SITE button control 414, the display of the roving electrode image 324 can show a current real-time position for the image 324 (as FIG. 9 depicts), or in a track view showing the path of movement for the image 324 over a period of time.

There are various ways to generate position-indicating information to track movement of the roving instrument relative to the basket 58.

b. Proximity sensing (Voltage Threshold Analysis)

In one embodiment (see FIG. 14), an electrical field F is established inside the body region S between an electrode 18 carried by the basket 58 an indifferent electrode 326, coupled to an electrical reference 328. The electrode 68 carried by the roving instrument 14 senses voltage amplitudes in the field F. The magnitude of a given sensed voltage amplitude $V_{SENSE}$ will vary according to location of the roving electrode 68 in the electric field F, and, in particular, to the distance between the transmitting basket electrode 18 and the roving electrode 68.

The sensed voltage amplitude $V_{SENSE}$ is compared to a threshold value $V_{THRESH}$. $V_{THRESH}$ is selected based upon empirical data to reflect a voltage amplitude that occurs, given the electrical conditions established, when a selected close-to-far transitional distance (e.g., 5 mm) exists between transmitting and sensing electrodes. If the sensed voltage amplitude $V_{SENSE}$ is equal to or greater than the threshold value $V_{THRESH}$, the roving electrode 68 is deemed to be in a "close condition" to the basket electrode 18 (e.g., closer than 5 mm). Otherwise, the roving electrode 68 is deemed to be in a "far condition" to the basket electrode 18.

Figure 14:
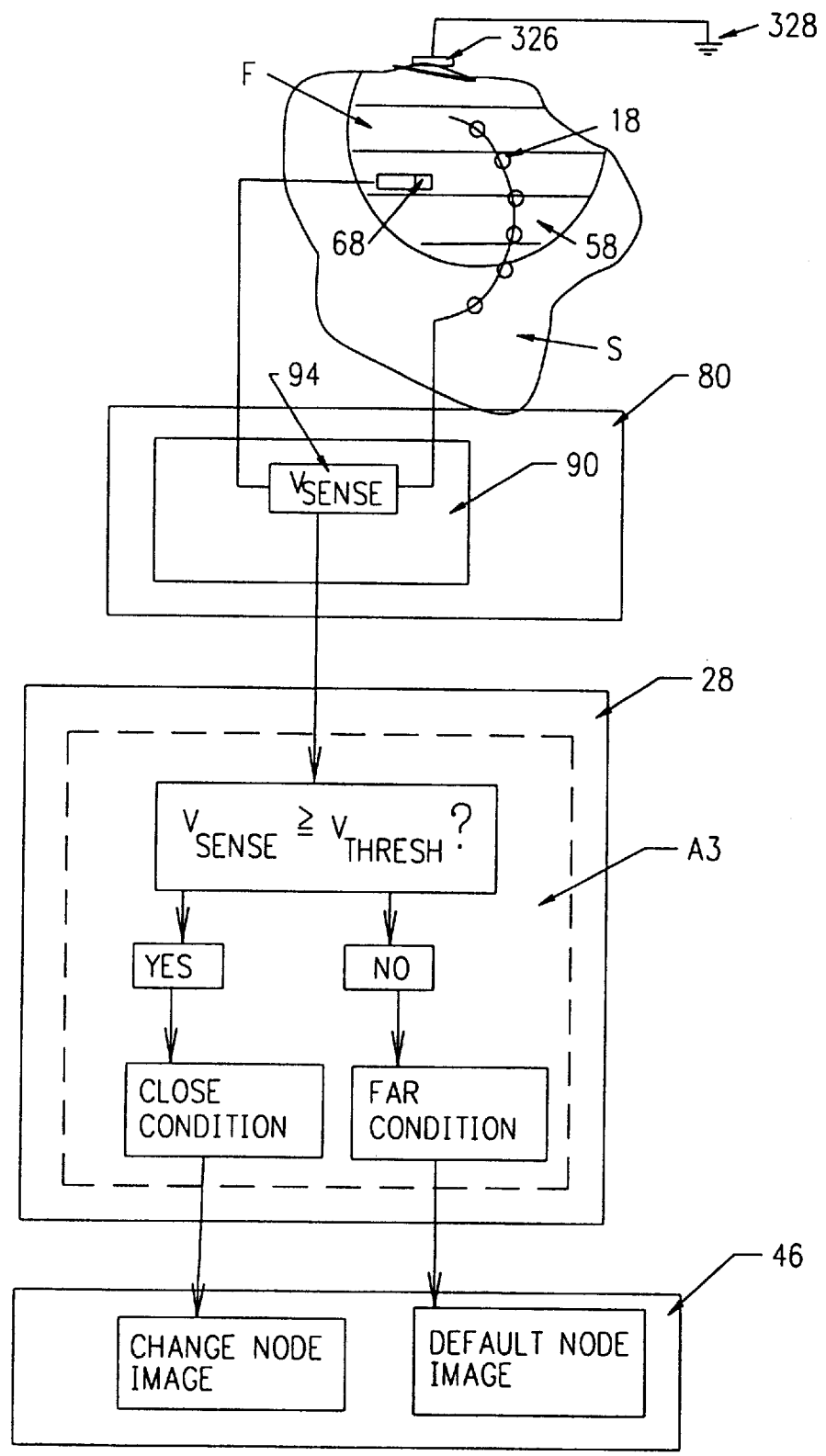
FIG. 14 is a schematic view showing the creation of proximity-indicating output for display by the virtual image navigation screen of the GUI.

Still referring to FIG. 14, the navigation application A3 can implement this methodology by initialized the electrode nodes N on the GUI 46 at a designated color or shade. The initialized color or shade for a given node N constitutes a default visual signal to the physician, that the roving electrode 68 is at the "far condition" relative to the associated basket electrode 18.

In the navigation mode, the switch manager 90 of the ASIC 80 periodically runs an algorithm from the embedded program 94, which assesses $V_{SENSE}$ for the roving electrode 68 relative to each electrode 18 on the basket 58. The manager 90 communicates the $V_{SENSE}$ values associated with each basket electrode 18 to the navigation application A3 executed by the MPU 28. The navigation application A3 compares each $V_{SENSE}$ to a selected $V_{THRESH}$. The navigation application A3 switches "ON" a given node N on the GUI 46, e.g., by changing the designated color, shape, or shade or by flashing the node N, whenever the comparison indicates that the roving electrode 68 is in a "Close Condition" relative to the electrode 18 to which the node N corresponds.

Figure 15:
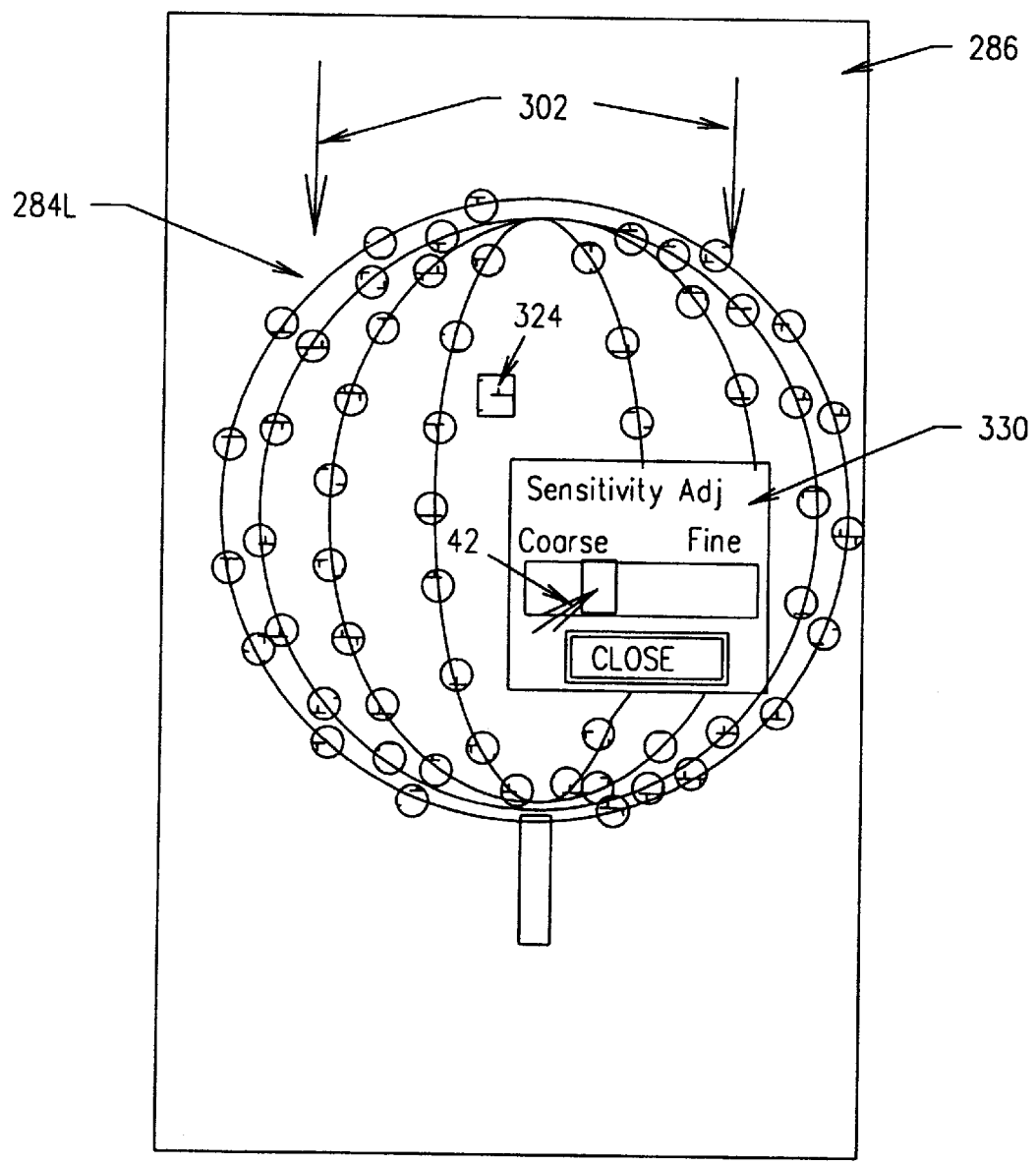
FIG. 15 is an enlarged view of an idealized image displayed by the virtual image navigation screen of the GUI, with the Sensitivity Adj dialog box displayed for adjusting sensitivity of the proximity-indicating output.

In a preferred embodiment, as FIG. 15 shows, the physician is able to select open a pop-up Sensitivity Adjustment Window 330. The Window 330 allows the physician to alter the spacial sensitivity for the proximity-indicating output, i.e, by changing the threshold value $V_{THRESH}$ used by the navigation application A3.

Figure 16:
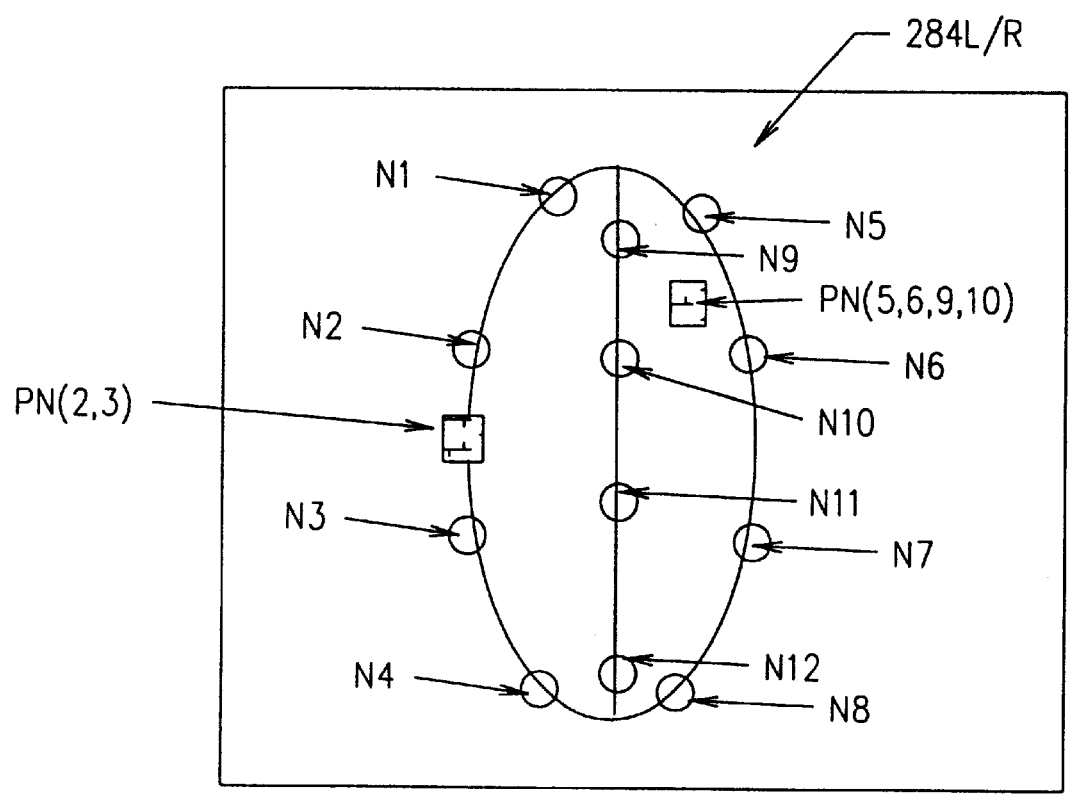
FIG. 16 is an enlarged view of an idealized image displayed by the virtual image navigation screen of the GUI, showing the interpolation of proximity-indicating output.

It is possible for more than one node to be switched "ON" at the same time, depending upon the orientation of the roving electrode 68 relative to the basket electrodes 18. In the illustrated embodiment (see FIG. 16), navigation application A3 interpolates the proximity-indicating outputs to switches "ON" a phantom node PN(2, 3) midway between two electrode nodes N2 and N3, each of which is in a "Close Condition" to the roving electrode 68. As FIG. 16 also shows, if more two nodes, e.g., N5, N6, N9, and N10 are ordered to be switched "ON" simultaneously, the navigation application A3 interpolates by switching "ON" a phantom node PN(5, 6, 9, 10) at the geometric center of the three or more electrode nodes N5, N6, N9, N10.

Further details of this manner of proximity sensing and display can be found in copending patent application Ser. No. 08/938,296, filed Sep. 26, 1997, and entitled "Systems and Methods for Generating Proximity-Indicating Output for Locating and Guiding Operative Elements within Interior Body Regions."

c. Spacial Sensing (Electrical Field Analysis)

Figure 17:
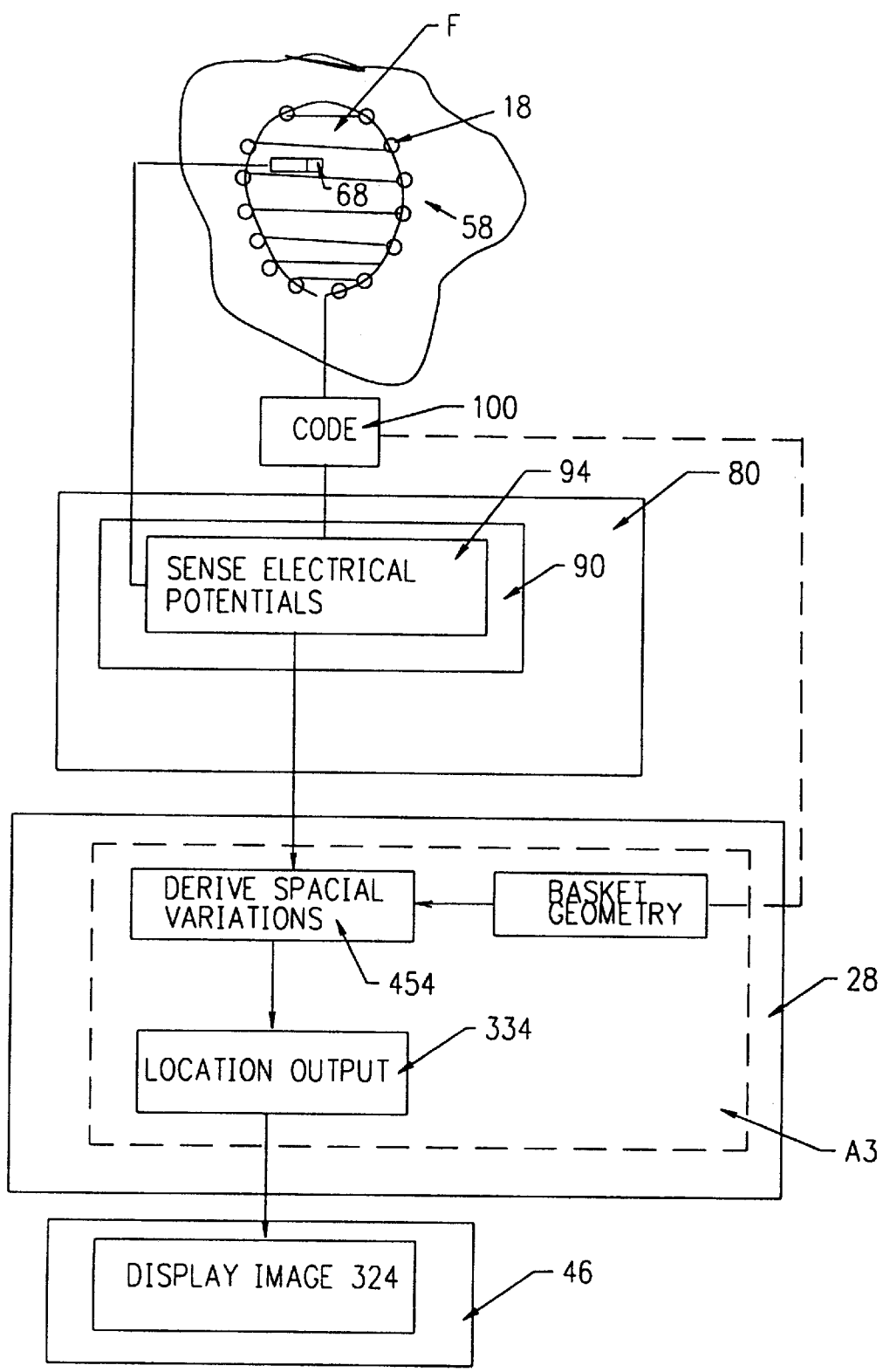
FIG. 17 is a schematic view showing the creation of location output based upon spacial variations in electrical potentials, for display by the virtual image navigation screen of the GUI.

Alternatively (see FIG. 17), when in the navigation mode, the algorithm of the program 94 embedded with the ASIC 80 can direct the switch manager 90 to generate an electrical field F from either the roving electrode 68 or at least one of the basket electrodes 30 (called the "transmitting electrode"). The electric field F will be characterized, in part, by the physical dimensions and spacing among basket electrodes 18.

The program 94 also directs the switch manager 90 to condition either the roving electrode 68 or at least one of the basket electrodes 18 to sense electrical potentials in the electric field, which will change based upon the position of the roving electrode 68 relative to basket electrodes 18. The sensed electrical potentials are communicated by the switch manager 90 to the navigation application A3.

The navigation application A3 includes an embedded navigation algorithm 454, which analyzes the spatial variations in the electrical potentials sensed within the field, in terms of, e.g., variations in phase, or variations in amplitude, or both, or variations in impedances between the transmitting and sensing electrodes. Knowing these spacial variations in the electrical field, and knowing the physical dimensions and spacing among basket electrodes 18 (which the identification code 100 of the basket 58 provides, or which can otherwise be embedded as empirically derived mathematical coefficients and weighing factors in the navigation algorithm 454), the navigation algorithm 454 generates a location output 334. The location output 334 locates the roving electrode 68 within the space defined by the basket 58, in terms of its position relative to the position of the multiple basket electrodes 18. The navigation application A3 updates the display by the GUI 46 of the moving electrode image 324 based upon the location output 334.

Further details of the use of an electrical field to sense and locate a movable electrode within an interior body region can be found in copending patent application Ser. No. 08/320,301, filed Oct. 11, 1994, and entitled "Systems and Methods for Guiding Movable Electrode Elements Within Multiple Electrode Structures."

d. Spacial sensing (Wave Form Analysis)

Figure 18:
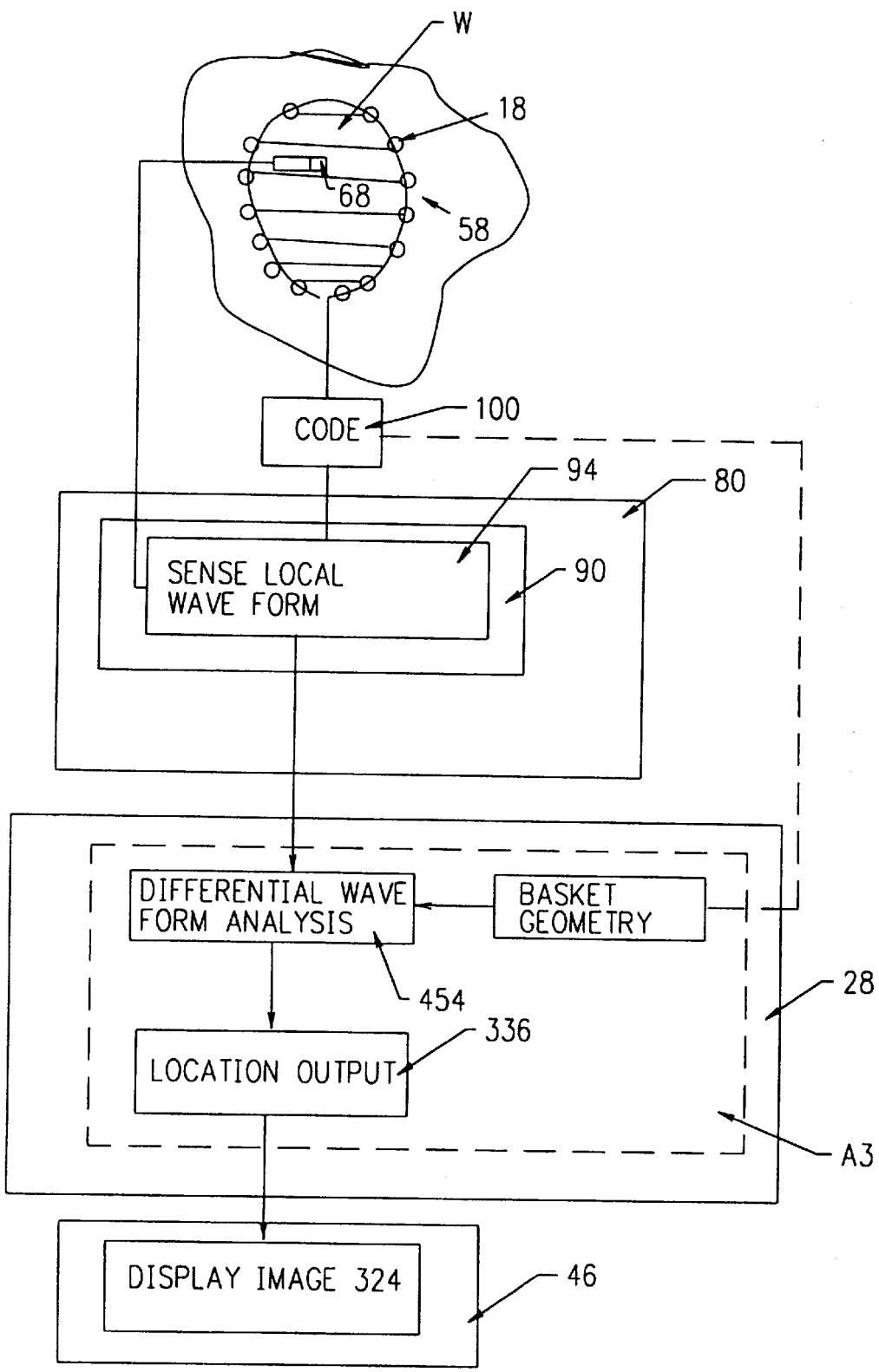
FIG. 18 is a schematic view showing the creation of location output based upon differential waveform analysis, for display by the virtual image navigation screen of the GUI.

In another alternative embodiment (see FIG. 18), when in the navigation mode, the algorithm of the program 94 embedded with the ASIC 80 can direct the switch manager 90 to generate an electric wave form output W from either the roving electrode 68 or at least one of the basket electrodes 30. The shape of the electric wave form output W within the basket 58 will be characterized, in part, by the physical dimensions and spacing among basket electrodes 18.

The program 94 also directs the switch manager 90 to condition the roving electrode 68 to periodically sense a local electric waveform. The manager 90 communicates the sensed local wave form to the navigation application A3. The navigation application A3 includes a navigation algorithm 454, which conducts a differential comparison of the waveform output and the sensed local waveform. Knowing the results of the differential waveform comparison, and knowing the physical dimensions and spacing among basket electrodes 18 (which the identification code 100 can provide or which can be otherwise embedded as empirically derived mathematical coefficients and weighing factors in the navigation algorithm 454), the navigation algorithm 454 generates a location output 336. The location output 336 expresses the position of the roving electrode 68 relative to the basket electrodes 18. The navigation application A3 updates the display the moving electrode image 324 on the GUI 46 based upon the location output 336.

Further details of the use of differential waveform analysis to sense and locate the position of a movable electrode within an interior body region can be found in copending patent application Ser. No. 08/745,795, filed Nov. 8, 1996, and entitled "Systems and Methods for Locating and Guiding Operating Elements Within Interior Body Regions."

6. Marking Navigation Data

In a preferred embodiment, the toolbar 296 of the navigation window an INS MARKER control button 390 and a FIND SITE control button 392. When selected, the control buttons 390 or 392 make it possible to annotate the displayed images 284L and 284R.

The INS MARKER control button 390, when selected, allows the operator to annotate either image 284L or 284R by adding an identifier or marker and an associated text comment to selected locations of the image 284L/R. When selected (see FIG. 19), the INS MARKER button 390 opens a Markers Control Menu 394. The Markers Control Menu 394 includes push button controls labeled ADD MARKERS 396, MOVE MARKERS 398, DEL MARKERS 400, and CLOSE 402.

When the ADD MARKERS button 396 is selected, the application A3 enables the operator to operate the pointing device 42 to select a spot on either image 284L or 284R and, by clicking, drop a shaped bitmap marker 404 (shown in FIG. 19) on the image. The marker 404 includes an associated number, which the application A3 assigns in numeric order as markers 404 are created. Once inserted in one image 204L or R, a corresponding marker 404 is automatically inserted in the other image.

Figure 19:
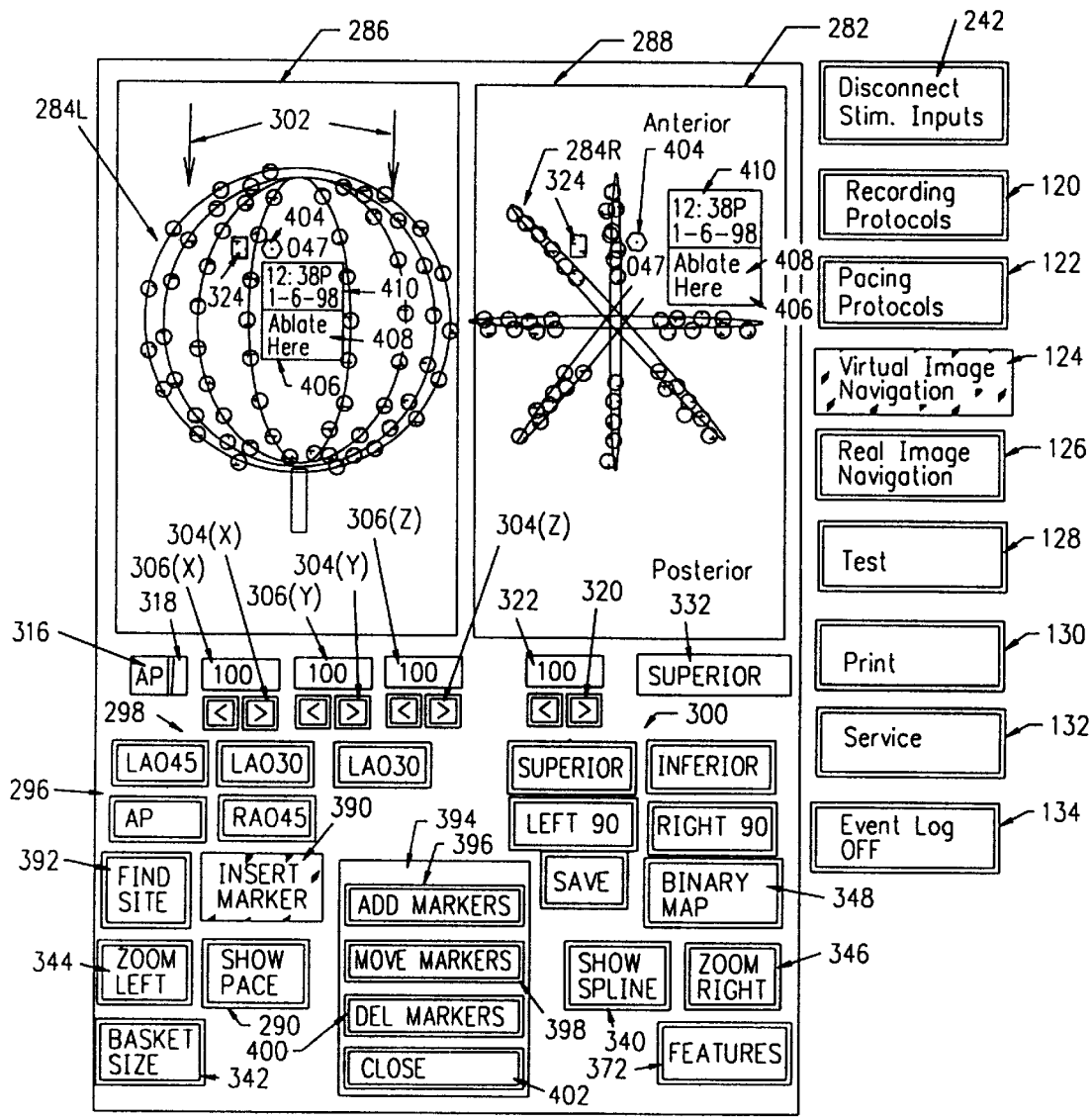
FIG. 19 is a depiction of the virtual image navigation screen of the GUI, with the Markers dialog box displayed.

As FIG. 19 shows, when the marker 404 is dropped into position on the image, the application A3 opens a pop up comments window 406. The window 406 includes an automatic time stamp 410 and an editable comments field 408. The operator enters the desired comment into the comment window 406 using the keyboard 40.

The markers 404 and comment windows 406 can be placed near electrodes nodes on either the foreground or background of the image 284L/R. The markers 404 and windows 406 mark selected locations that are significant or of interest, such as mapping sites, ablation sites, etc. The physician is thereby better able to remain coordinated and oriented with the displayed image and, therefore, better able to interpret data recovered by the basket 58.

When the marker control menu 394 is displayed, the application A3 removes a selected marker 404 and associated comment window 406 when the DEL MARKER button 400 is selected. The MOVE MARKERS button 398, when selected, allow the operator to drag and then drop a selected marker 404 and associated comment window 406 to a different location on the image 284L/R.

Selecting the CLOSE button 402 dismisses the marker control menu 394. The marker(s) 404 and comment window (s) 406 remain on the image 284L/R. Selecting the SAVE button 314 on the toolbar 296, as previously described, saves the image 284L/R together with all current markers 404 and comment windows 406. Information resident on the entire graphical display, including model image 284L/R, markers 404, and associated comment windows 408 are saved as a data file records for storage, retrieval, or manipulation.

Figure 20:
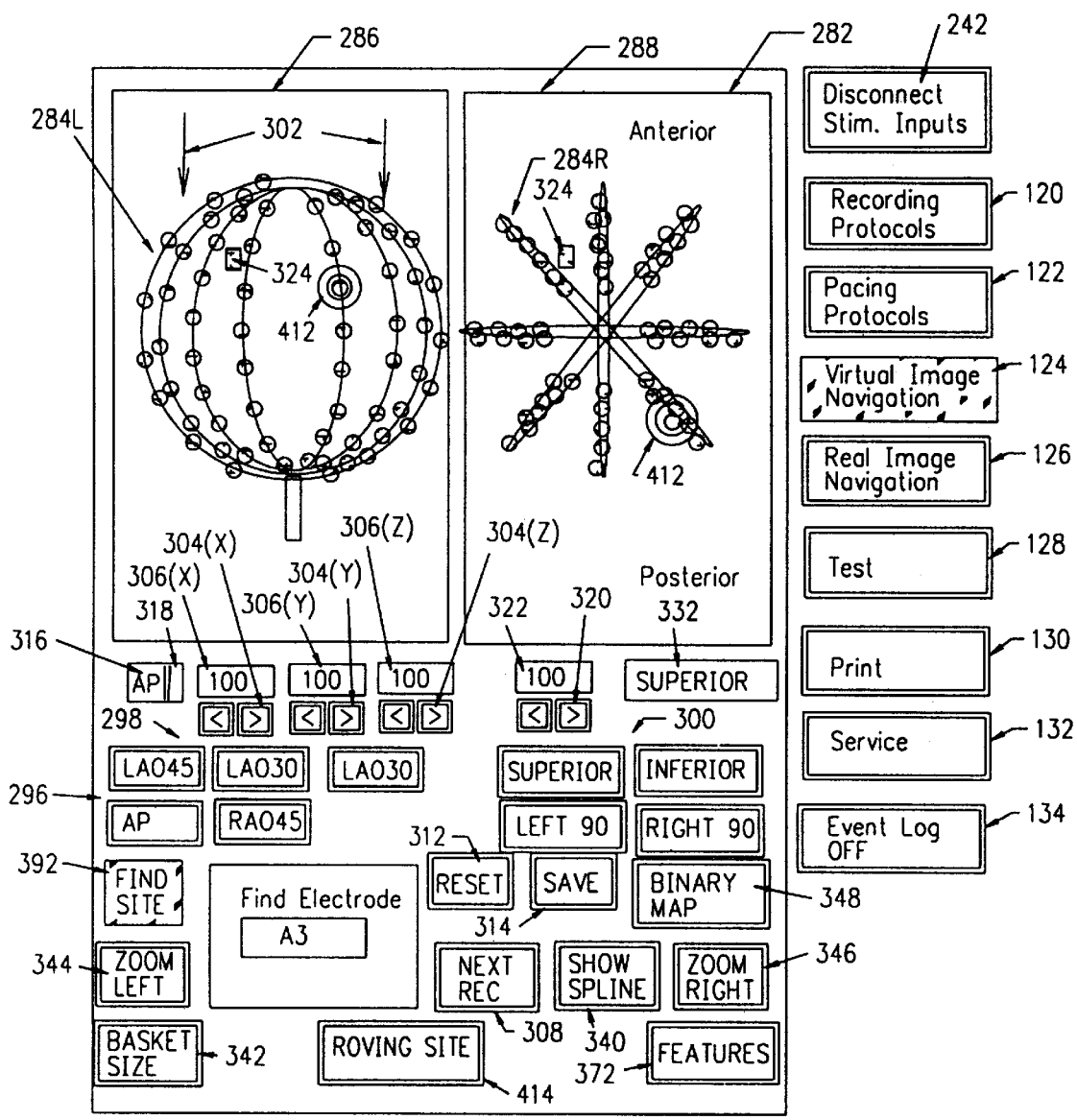
FIG. 20 is a depiction of the virtual image navigation screen of the GUI, with the Find Site dialog box displayed.

Selecting the FIND SITE button 392 opens a dialog box 410 (see FIG. 20), into which the operator enters an electrode coordinate (A1, B6, etc.). The navigation application A3 draws a flashing circle 412 about the corresponding electrode node on both images 284L/R. The flashing circle 412 remains on the image until another action is taken by the operator.

7. Real Image Navigation Application (A4)

The selection of the REAL IMAGE NAVIGATION push button control 126 runs the real image navigation application A4. The application A4, when executed by the MPU 28, displays a sub-window 416, as shown in FIG. 21, which displays in real-time the image 418 acquired by the imaging device 72.

Figure 21:
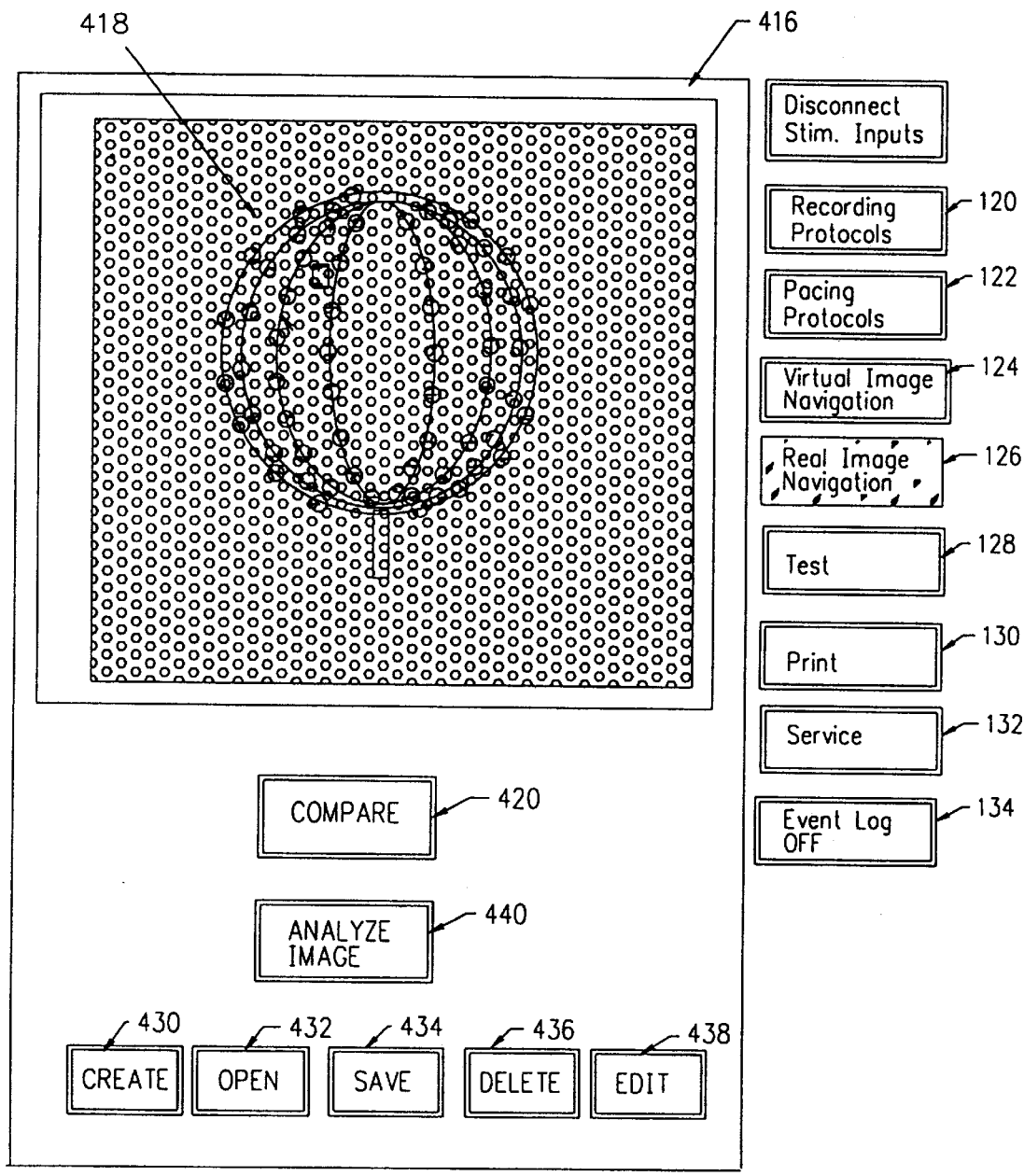
FIG. 21 is a depiction of the real image navigation screen of the GUI.

As can be seen in FIG. 21, the main application control push buttons 120 to 134 still remain in view on the right side of the screen in their original first color, except the selected REAL IMAGE NAVIGATION push button control 126, which changes color when selected.

The application allows the operator to process the image 418 in various ways to achieve different results.

a. Image Comparison

The sub-window 416 of the application A4 displays the image 416 acquired by the fluoroscope or other imaging device 72. This image 416 may be used in association with the virtual image navigation application A3 to help visualize the actual orientation of the basket 58 and roving electrode 68 in the body region.

The sub-window 416 includes a COMPARE control button 420. When selected, the visualize application switches to a new sub-window 422 (see FIG. 22, which displays in a left panel 424 the left panel image 284L of the virtual navigation sub-window 282(generated by the application A3 previously discussed) along with a right panel 426, in which the real-time image 418 is displayed. The orientation control buttons 304 (X,Y,Z) and 320 and associated numeric orientation angle fields 306 (X, Y, Z) and 322 present on the virtual image navigation screen 282 are also displayed in the compare window 422. This presentation allows the physician to compare the fluoroscopic or other independent image and manipulate the GUI image 284L to more closely match the view of the real-time image 418. The images 284L and R displayed on the virtual image navigation screen 282 (see FIG. 9) are updates to reflect changes in orientation made using the compare screen 422.

Figure 22:
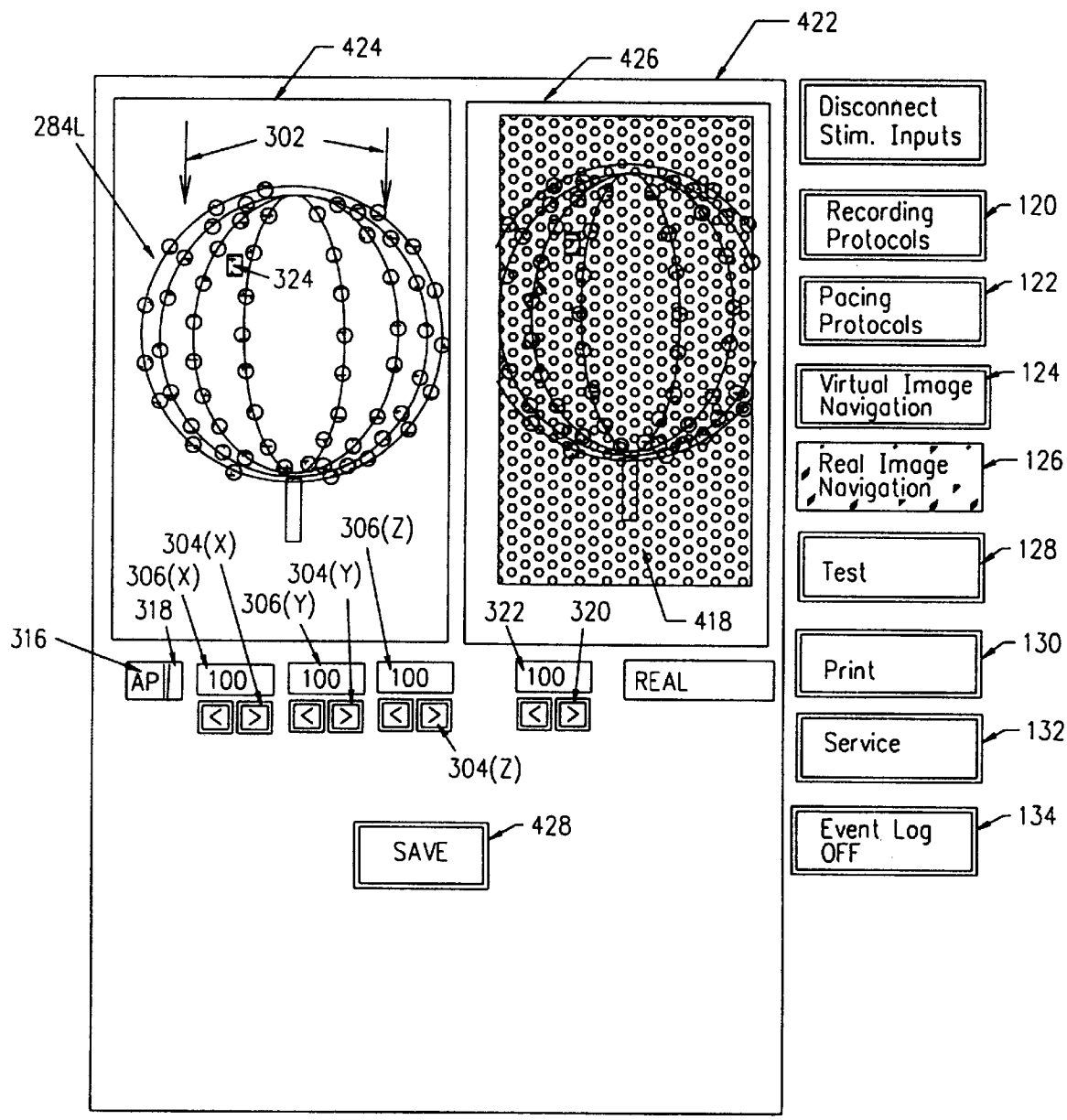
FIG. 22 is a depiction of the real image navigation screen of the GUI, with the compare image function enabled.

In a preferred embodiment, the applications A3 and A4 permit point-and-drag control by the pointing device 42, to change the shape of the idealized image 284L on either navigation screen 282 or 422, to more closely match the shape of the image 418 as seen in the real-time image panel 426, or using an independent real time imaging system. The shape of the idealized image 284L can be formed by dragging the pointing device 42, for example, to appear in a range of configurations from spherical to a more elongated ellipsoid (when the image 284L depicts a three-dimensional basket 58, as shown in FIG. 22) or to appear in a range of curve radii, when the multiple electrode instrument 12 comprises an elongated, curvilinear structure.

The compare windows 422 includes a SAVE control button 428. When selected, the SAVE button 428 saves the shape characteristic formed by the physician in the compare window 422, along with other image information, as already discussed. Once the idealized image 284L/R are coordinated with the real image 418 through use of the compare window 422, the physician can switch views of the idealized image 284L/R electronically on the navigation screen 282, without further manipulating the real-time imaging device 72.

b. Image Processing

The sub-window 416 of the application A4 (see FIG. 21) also includes specialized file management control buttons, labeled CREATE 430, OPEN 432, SAVE 434, DELETE 436, and EDIT 438.

When the CREATE control button 430 is selected, the application A4 freezes the real-time image 416 (or a prescribed sequence of video images 416) so that it can be grabbed for processing. When the EDIT control button 438 is selected, the operator can mark or annotate the grabbed image or video image sequence with comments, in the same manner permitted by the INS MARKER button 390 of application A3, which has been previously described (see FIG. 19).

When the SAVE control button 434 is selected, the grabbed image or video image sequences, with annotations, can be saved to the hard drive as a data base record file, preferably as part of the patient data base 52, which will be described in greater detail later.

Because real time image files are typically large (e.g. exceeding 50 KB), various compression methods can be used to compress them and thus, save disk space. The compression can be lossy (i.e. when data are retrieved some information may be lost) or lossless (i.e. no data are lost upon retrieval). The compression ratios are higher for lossy compression. For fluoroscopy and ultrasound images, minor data loss is acceptable upon retrieval. In a preferred embodiment, real time video data are stored into patient database 32 using optimal lossy compression. Once saved into the database 32, these images and annotations can be retrieved by selecting the OPEN button 432 for future analyses. The images and annotations, once opened, can be further annotated by selecting the EDIT button 438 (which recalls the MARKERS function), or can be removed from the data base 32 by selecting the DELETE button 436.

c. Image Analysis

The sub-window 416 of the application A4 (see FIG. 21) also includes an ANALYZE IMAGE control button 440. When selected (see FIG. 23), the application A4 executes an embedded graphic analysis function 442. The function 442 electronically process the video input signals 458 to mathematically generate digital three-dimensional basket coordinates 450 and three-dimensional roving electrode coordinates 452. The digital coordinates 450 and 452 are communicated to the navigation processing algorithm 454 of the application A3 to help construct the idealized image 284L/R displayed on the navigation screen 282.

In the illustrated embodiment (see FIG. 23), the basket electrodes 18 and splines and the roving electrode 68 are visualized from two different angles using a biplane fluoroscopy unit 444. The unit 444 includes one fluoro arm 446, which captures a real AP (anterior-posterior) video image, and a second fluoro arm 448, which captures either a real LAO90 (left-anterior-oblique) image or a real RAO90 (right-anterior-oblique) image of the basket 58. These images are processed through the interface 26 as the video signal inputs 458 to the application A4.

At the same time, the imbedded navigation algorithm 94 in the interface 26 (previously described) receives from the basket electrodes 18 and the roving electrode 68 electrical position-indicating signals. The interface 26 conveys these as electrical signal inputs 456 to the navigation processing algorithm 454 executed by the application A3. As previously described, when the real image analysis function 442 is not enabled, the navigational outputs 334/336 of this algorithm 454 are displayed in graphical form on the image 284L/R.

When enabled by selection of the ANALYZE IMAGE control button 440, the image analysis function 442, the analysis function 442 mathematically computes, based up the video input signals 458, three-dimensional digital basket coordinates 450. The digital coordinates 450 are inputted to the navigation processing algorithm 454 of the application A3. The application A3 generates a basket image output 466 that takes the real image basket coordinates 450 into account, thereby providing an idealized image 284L/R that more closely corresponds to the real image 418.

Figure 23:
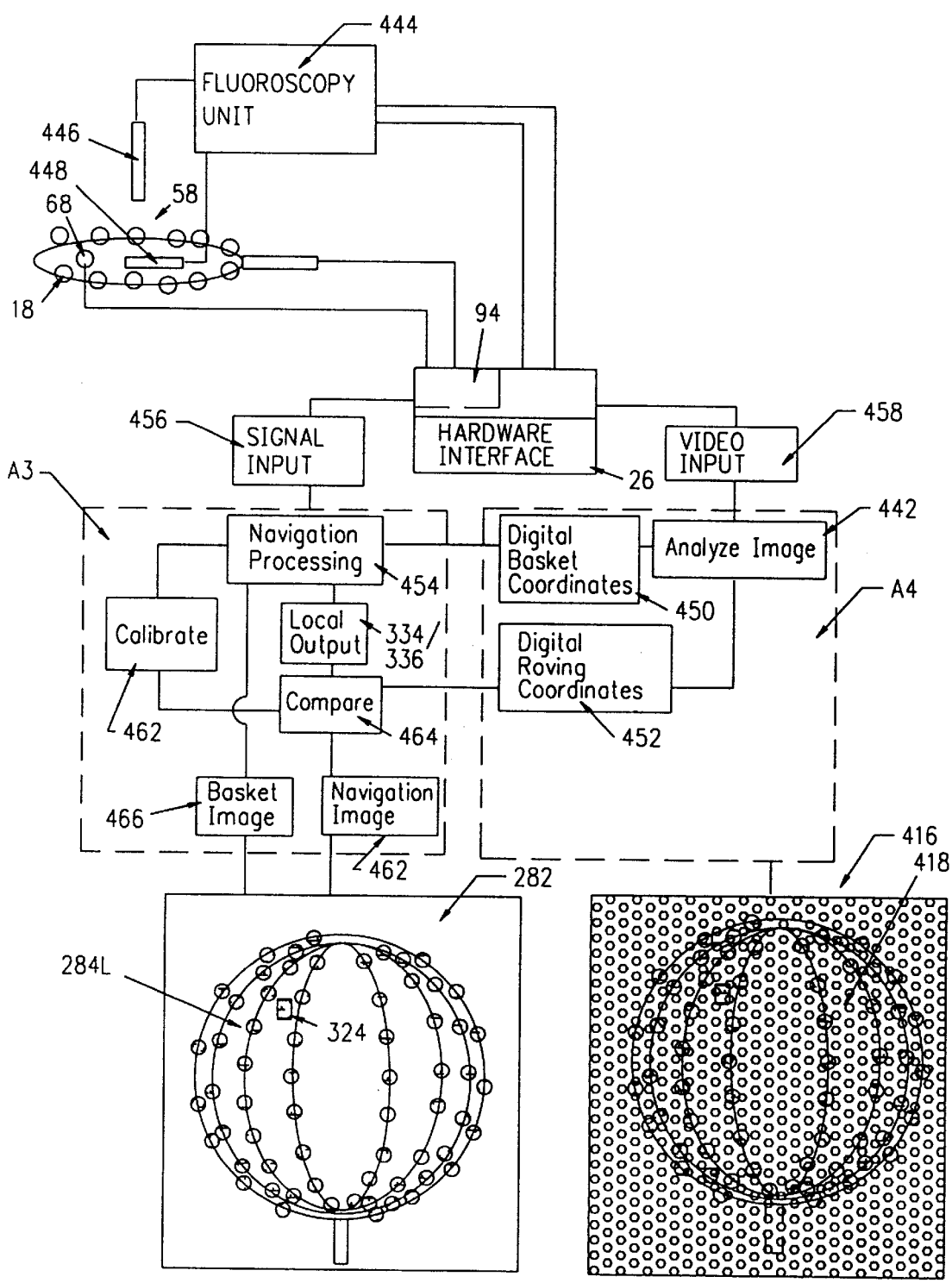
FIG. 23 is a schematic showing an implementation of the analyze image function.

As FIG. 23 also shows, when enabled, the analysis function 442 also generates, based upon the real image of the roving electrode 68, three-dimensional roving digital coordinates 452. The application A3 includes a comparator 464, which compares the three-dimensional digital roving coordinates 452 to the location output (e.g., 334 or 336) generated by the navigation algorithm 454, as previously described (see FIG. 17 or FIG. 18). The error output of the comparator 464 is communicated to an iterative calibration loop 460, which adjusts empirically initialized mathematical coefficients and weighing factors assigned to the navigation algorithm 454 to minimize comparison errors. The analysis function 442 thereby provides a self-calibration feature for navigation algorithm 454 of the application A3. The calibrated output 462 is used to construct the display of navigational information on the navigation screen 282.

8. Test Application (AS)

Figure 24:
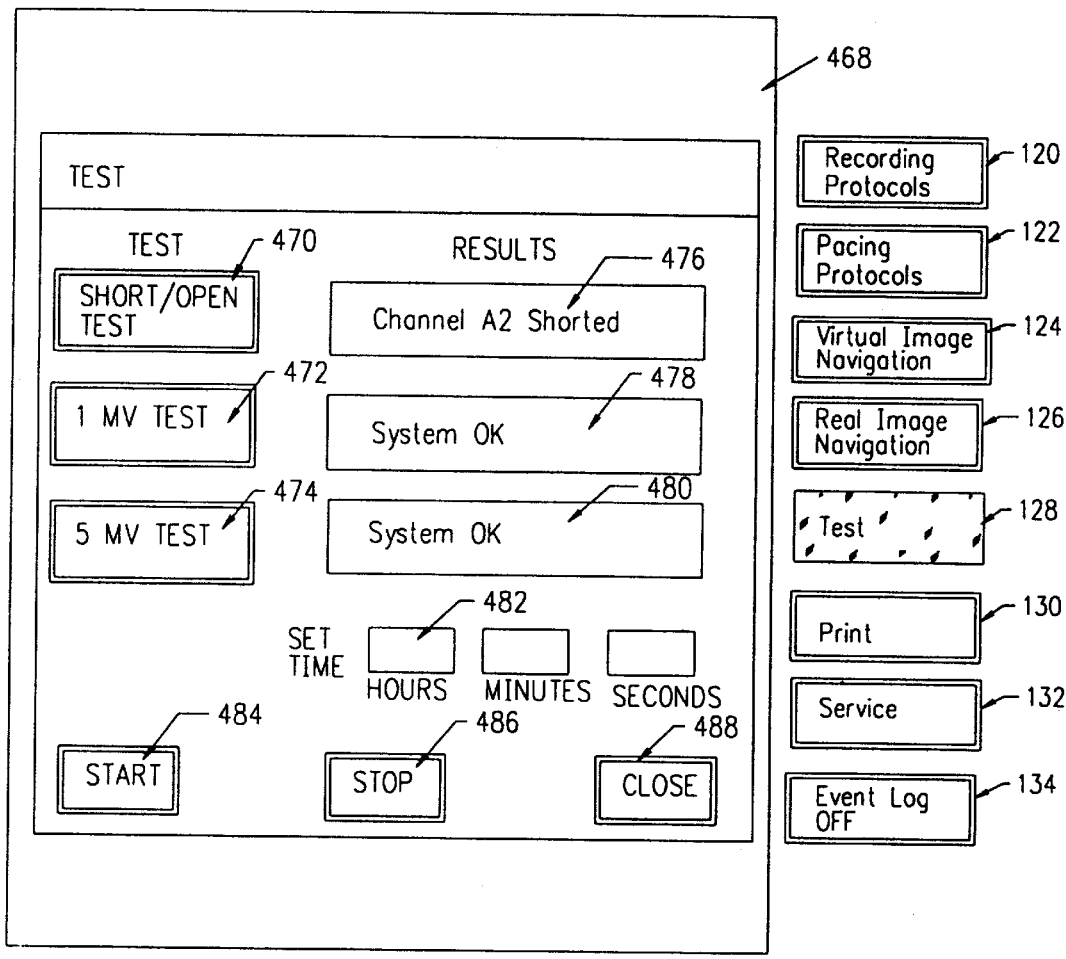
FIG. 24 is a depiction of the test screen of the GUI.

The selection of the TEST push button control 128 runs the test application A5. The test application A5, when executed by the MPU 28, displays the test sub-window 468, as shown in FIG. 24. As can be seen in FIG. 24, the main control push buttons 120 to 134 continue to remain in view on the right side of the window 468 in their original first color, except the selected TEST push button control 128, which changes color when selected.

The test application A5, when executed, conditions the switch manager 90 to apply voltage among the various electrodes 18 and recorder input channels 116 (see FIG. 3)to verify the ability to operate according to the configuration specified in the Record Configuration window 136 (shown in FIG. 5). The test application A5 executes a short/open channel test at each input channel pair specified by the operator on the test sub-window 468. The test application A5 displays the results of the test.

The test application A5 also allows the operator to set the local system time.

In the illustrated embodiment (see FIG. 24), the test sub-window 468 includes a SHORT/OPEN TEST push button control 470, a 1 MV TEST push button control 472, and a 5MV TEST push button control 474. The sub-window also includes a RESULTS data fields 476, 478, 480 aligned with each test push button control 470, 472, and 474. The sub-window 468 also includes an editable SET TIME data field 482 in HH:MM:SS format.

A START push button control 484 (to start a selected test), a STOP push button control 486 (to stop a selected test), and a CLOSE push button control 488 (to terminal all selected tests and close the test sub-window 468) are also displayed on the test sub-window 468.

a. Short/Open Test

In executing a Short/Open Test, the detection of shorted and open electrodes can be performed either "exhaustively" or by specifying particular pairs of inputs and outputs. In the "exhaustive" test, all possible combinations of input and output pins are tested. Although effective in finding all potential malfunctions, such a test takes considerable time. Alternatively, the test can be conducted only between specified pairs of inputs and outputs. Operating speed is considerably increased using such a test protocol.

Upon selection of the SHORT/OPEN TEST button 470 and the START button 484, the test application A5 configures the switch manager 90 to detect open or shorted electrodes. In the illustrated embodiment, the ASIC 80 includes a constant current source 490 (see FIG. 3), which can be selectively switched to each of the electrodes 18 and 68 coupled to the interface 26.

Generally speaking, if the electrode 18/68 is outside the patient's body, a voltage condition above a specified high threshold will result when the constant current source is coupled to an open electrode. A detector 492 on the ASIC 80 (see FIG. 3) senses the occurrence of the high voltage. The detector 492 can also check whether the phase angle is greater than a predetermined limit (e.g., 45°). If prescribed criteria are met, the switch manager 90 returns an Open Electrode signal to the test application A5. The test application generates an Open Electrode message in the associated RESULTS data field 476. The test application A5 also updates the STATUS field 166 in the recording configuration window 136 (see FIG. 5) and the STATUS field 226 in the pacing configuration window 208 (see FIG. 7) indicate an opened electrode condition.

Generally speaking, if the electrode 18/68 is inside the patient's body, a low voltage condition below a specified low voltage threshold results when the constant current source 490 is coupled to a shorted electrode. The detector 492 senses the low voltage condition. The detector 492 can also check whether the phase angle meets various criteria. If prescribed criteria are met, the switch manager 90 returns a Shorted Electrode signal to the test application A5. The test application generates a Shorted Electrode message in the associated RESULTS data field 476. The test application A5 also updates the STATUS field 166 in the recording configuration window 136 (see FIG. 5) and the STATUS field 226 in the pacing configuration window 208 (see FIG. 7) indicate a shorted electrode condition.

Further details regarding the Short/Open test criteria for the ASIC can be found in copending patent application Ser. No. 08/770,971, filed Dec. 20, 1996, and entitled "Unified Switching System for Electrophysiological Stimulation and Signal Recording and Analysis," which is incorporated herein by reference.

The absence of an Open Electrode signal and a Shorted Electrode signal is interpreted by the test application A5 as an operational electrode. The test application A5 generates a operational electrode message in the associated RESULTS data field 476. The absence of information in the STATUS fields 166 and 226 in the recording configuration window 136 and the pacing configuration window 208 likewise indicates an operational electrode condition.

b. High/Low Voltage Tests

Upon selection of the lMV TEST button 472 and the START button 484, the test application A5 configures the switch manager 90 to output a low (1 mV) electrical level for a set period of time to the electrodes. Likewise, upon selection of the 5 MV TEST button 474 and the START button 484, the test application A5 configures the switch manager 90 to output a high (5 mV) electrical level for a set period of time to the electrodes.

To accommodate these test procedures, the ASIC 80 includes a high voltage source 494 and a low voltage source 496 (see FIG. 3), which are coupled to the outputs when so commanded by the test application A5. The voltages thus applied are sensed at the associated electrodes. The absence of the sensed voltages, or the sensing of different voltage values, indicates a faulty condition in the hardware interface 26. The test application A5 generates a an appropriate message in the associated RESULTS data fields 478 or 480.

9. Print Application (A6)

Figure 25:
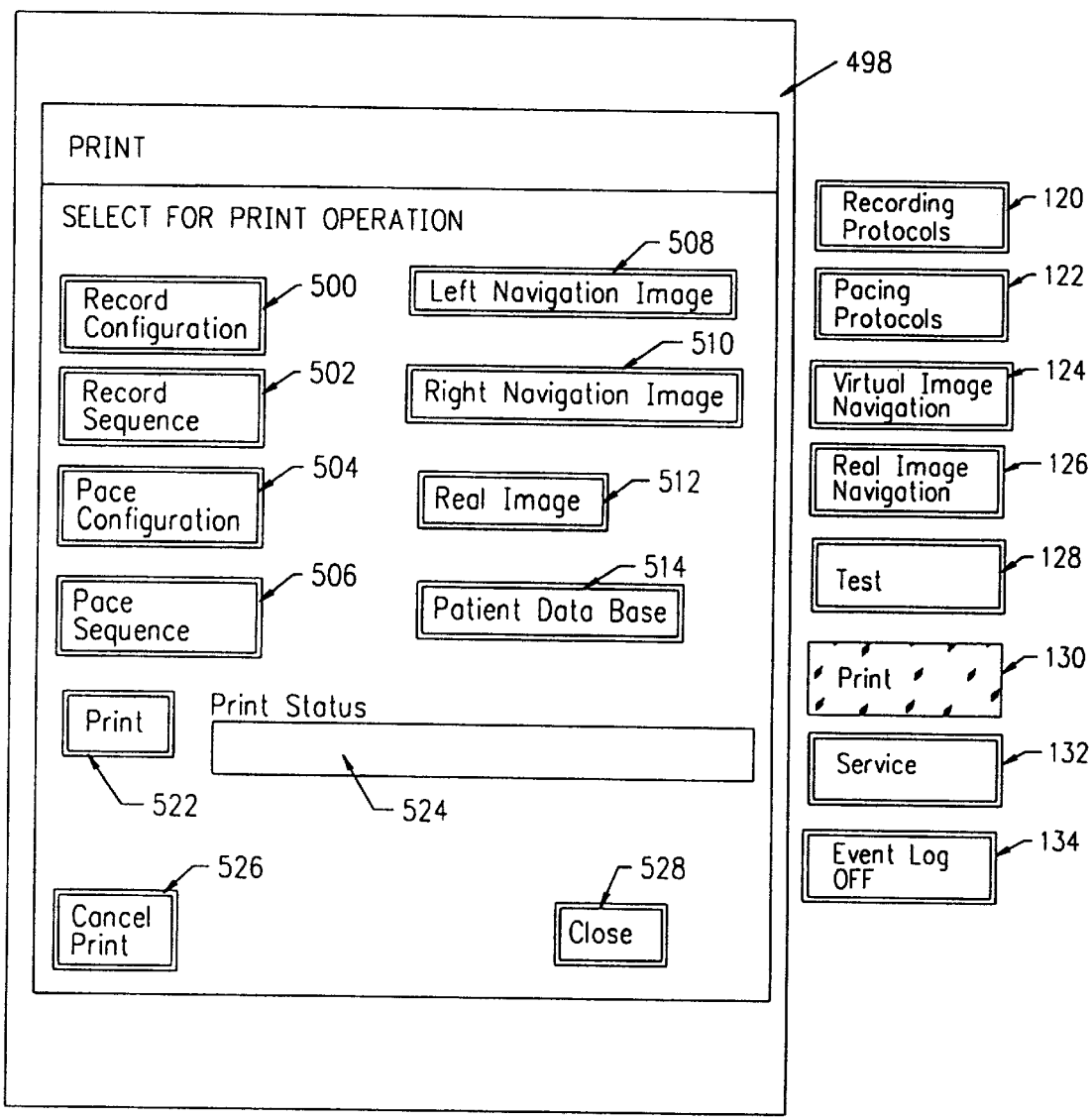
FIG. 25 is a depiction of the print screen of the GUI.

The selection of the PRINT push button control 130 runs the print application A6. The print application A6, when executed by the MPU 28, displays the pint sub-window 498, as shown in FIG. 25. The main control push buttons 120 to 134 continue to remain in view on the right side of the print window 498 in their original first color, except the selected PRINT push button control 130, which changes color when selected.

The print window 498 provides an array of push button controls, which permits the operator to select, by keyboard entry or pointing device 42, one or more screen displays to be printed on the printer. For example, the illustrated embodiment offers the buttons labeled for the following print selections: Record Configuration information 500, Record Sequence information 502, Pace Configuration information 504, Pace Sequence information 506, the Left Navigational Image 508, the Right Navigational Image 510; the Real Image Freeze 512; all or selected data base items of the Patient Data Base 514(as will be described later).

When the PRINT control button 522 is selected, the print application A6 compiles and formats the selected information for output to the printer 34. The print application A6 also appends pre-designated patient information from the data base to the printout.

After a printing operation has begun, the print application A6 displays status information in a PRINT STATUS field 524. A CANCEL PRINT button control 526 allows the operator to cancel the current printing operation. The CLOSE control button 528 dismisses the print window 498 and returns control to the application being executed at the time the PRINT button 130 was selected.

10. Service Application (A7)

Figure 26:
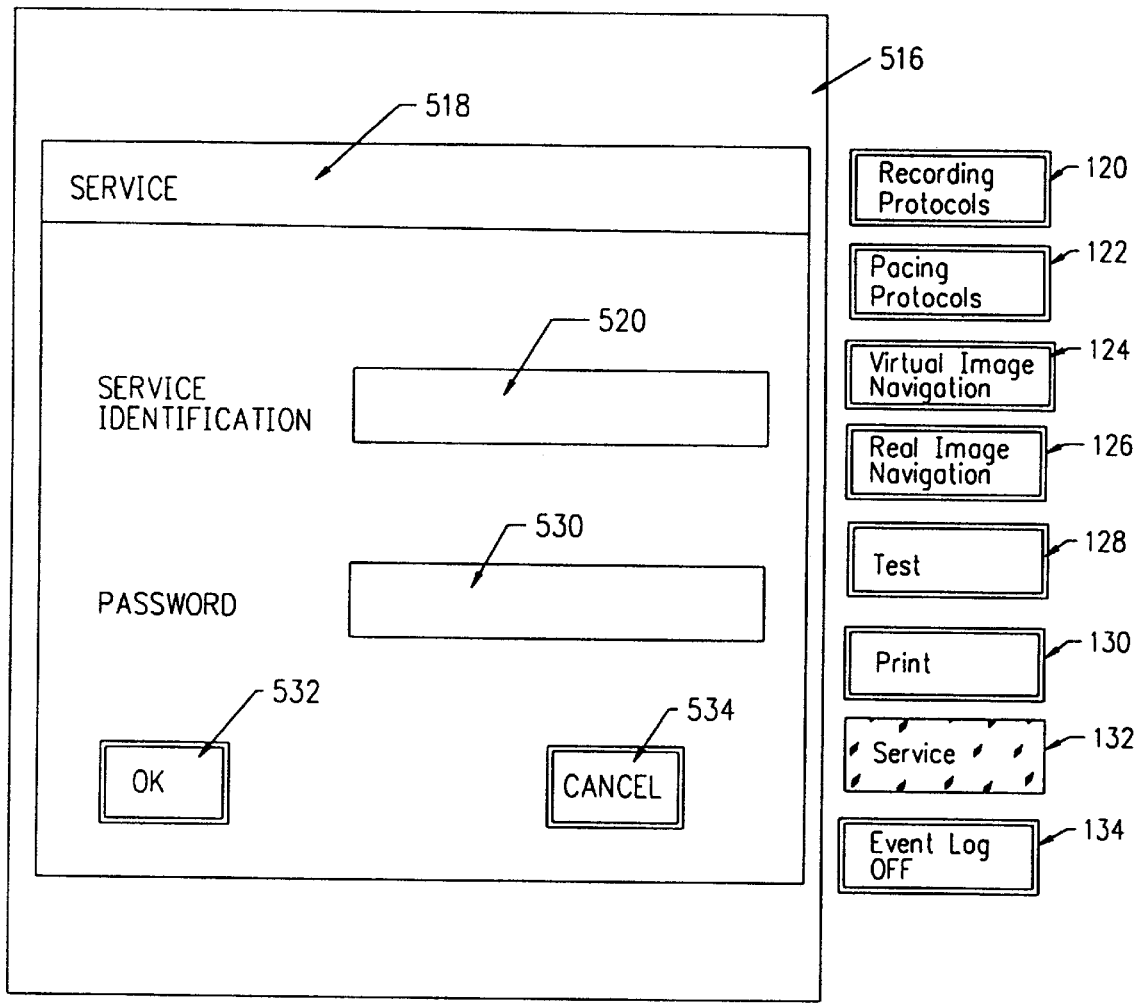
FIG. 26 is a depiction of the service screen of the GUI.

The selection of the SERVICE push button control 132 runs the service application A7. The service application A7, when executed by the MPU 28, displays the service sub-window 516, as shown in FIG. 26. The main control push buttons 120 to 134 remain in view on the right side of the window 516 in their original first color, except the selected SERVICE push button control 132, which changes color when selected.

The service window 516 displays a dialog box 518, which contains input fields for the operator to enter a SERVICE IDENTIFICATION 520 and a PASSWORD 530. When the OKAY button 532 is selected, the service application A7 accepts the inputs in the fields 520 and 530 and compares them to known identification and password codes embedded in the application A7. When the inputs match the known codes, the service application A7 terminates the GUI 46 and returns control of the MPU 28 to the underlying operating system 44. The service application A7 provides access to the underlying operating system 44 and associated host computer functions only to authorized service personnel.

Selection of the CANCEL button 534 dismisses the service window 516 and returns control to the application being executed at the time the SERVICE button 132 was selected.

11. The Event Log Function (F1)

The operating system includes an Event Log Function F1 (see FIG. 1), which retains in system memory a record of specified critical events as they occur during the course of a given procedure. For example, in the illustrated embodiment, critical events can include: the selection of the APPLY control button 160 in the Recording Configuration window 136 (FIG. 5); the selection of the APPLY control button 240 in the Pacing Configuration window 208 (FIG. 7); changes in the configuration of the pacing electrodes shown in the configuration control window 208 (FIG. 7); the times at which the switch manager 90 applies a configured record sequence or a configured pace configuration; and the selection of the DISCONNECT STIMULATOR button control 242.

In the illustrated embodiment, the Event Log Function F1 records the specified events by time (read from the operating system 44) in the event log 50 (see FIG. 1). The event log data base 50 indexes the recorded events according to patient information, the coordinates of the roving instrument, the recording configuration name, the pacing electrodes, and comments (which identify the nature of the event).

Figure 27:
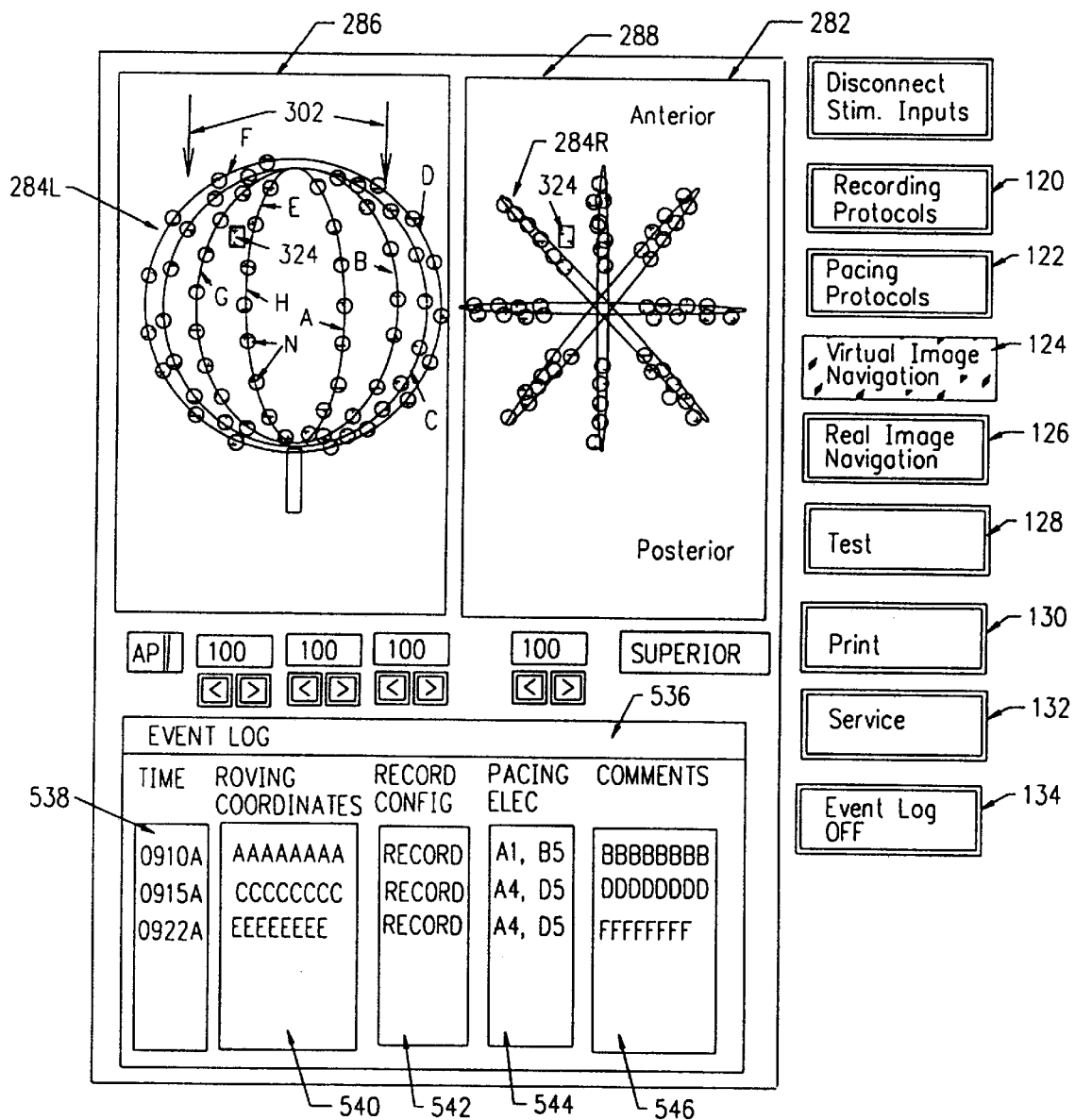
FIG. 27 is a depiction of the virtual image navigation screen of the GUI, with the Event Log control button function toggled on to display the Event Log.

The selection of the EVENT LOG control button 134 toggles display of the contents of event log for the current session on and off. When the control button is selected on, a pop-up window 536 is displayed on the navigation screen 282 (see FIG. 27). The pop-up window 282 has data field entries, provided from the event log data base 50, which are arranged under headers for Time 538, Roving Instrument Coordinates 540, Recording Configuration Name 542, Pacing Electrodes 544, and Comments 546. When active, the operator can input additional information in the Comment field 546. When the control button 134 is selected off, the pop-up window is not displayed, although the Event Log Function F1 still continues to record events in the event log data file 50.

12. Patient Data Base Function (F2)

In the illustrated embodiment (see FIG. 1), the operating system 44 includes a Patient Data Base function F2. The function F2 makes it possible, during the course of a given procedure, to store, retrieve, and manipulate patient-specific and related procedure-specific information in a patient data base 52 resident on the hard drive 32. The Patient Data Base function F2 creates data base items incorporating patient-specific and related procedure specific information, comprising, e.g., patient name and other identifying information, together with navigation images 284L/R generated by the navigation application A3; the threshold sensitivity set using the Sensitivity Adjustment window 330 in the navigation application A3 (see FIG. 15); catheter configuration and recording configuration and sequences generated by the recording protocols application A1; pacing configuration and sequences generated by the pacing protocols application A2; physician's comments and annotations inserted by use of the Markers Control Menu 394 in the navigation application A3 (see FIG. 19); anatomic features positions inserted using the Features button 372 in the navigation application A3 (see FIGS. 9 and 13); mapping information generated through use of the binary map selection menu 368 by the navigation application A3 (see FIGS. 11 and 12); contents of the Event Log 50; and fluoroscopy, ultrasound, or other medical images generated by the real image application A4 (see FIG. 21).

The Patient Data Base function F2 compiles patient-specific and procedure-specific information as disk files saved to the hard disk 32. The disk files in the data base 52 are organized in study subdirectories based upon the patient's name. The data base items can also be manipulated by the operator, e.g., selected data base files can be accessed or opened upon command for editing, deletion, searching, listing, sorting, compiling, and printing.

a. Establishing Patient Data Base Information

Figure 28:
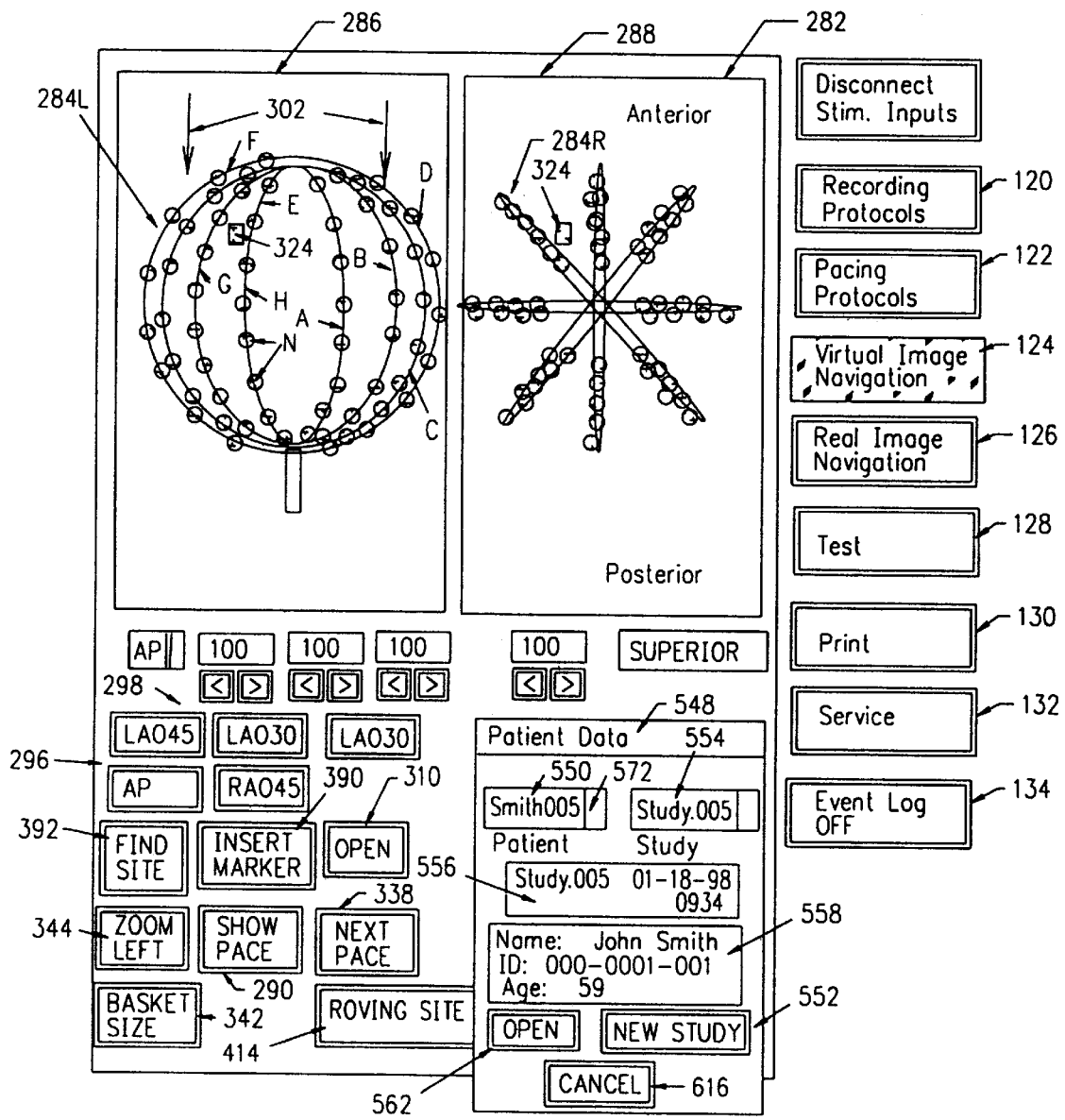
FIG. 28 is a depiction of the virtual image navigation screen of the GUI, with the Patient Data Base function enabled and the Patient Data dialog box opened for data input at the outset of a new study.

The Patient Data Base function F2 can be implemented in various ways. In the illustrated embodiment, the Patient Data Base function F2 opens a Patient Data Window 548 (see FIG. 28) at the time that the Toolbar 296 (previously described) is first generated by the navigation application A3 in the course of a given procedure, as this event occurs at the beginning of a given study.

The Patient Data Window 548, when opened, requires the physician to enter data about the particular patient and procedure, to thereby establish a new patient/study subdirectory in the data base 52, before the new study is allowed to proceed. Selecting the Cancel button 616 dismisses the Data Window 548 without establishing a new patient/study subdirectory, returning the operator to the navigation window 282 for the current study.

To create a new patient/study subdirectory in the data base 52, and thereby enable the new study to proceed, the physician enters the name of the patient and a numeric three digit sequence number in a Patient field 550 of the Data Window 548. The Patient field 550 includes a drop down menu control 572, listing existing patient names from which the operator can select. Once the name is entered, the function F2 detects existing subdirectories for the same name and creates an addition study subdirectory, or otherwise a new patient directory is established and the new study subdirectory created. The function F2 assigns a name to the new study in a Study Name field 554, with an associated time marker 556. The patient three digit numeric sequence serves as a study name extension.

The physician can enter in the Text field 558 of the Data Window 548 additional information or comments regarding the patient, such as the patient's ID number, age, etc., which the physician wants to save as part of the patient/study record. The physician can also enter diagnostic information, e.g., heart tissue pacing data; or therapeutic information, e.g., heart tissue ablation data; or identify the attending physician or staff personnel. The Data Window 548 includes an Open Button 562, which recalls the most recent study record for the patient, and inserts information in the Text field 558 of the existing record into the Text field 558 of the new study record.

The physician clicks the New Study button 552 of the Data Window 548. The function F2 automatically saves the patient/study information to the newly created subdirectory.

Figure 29:
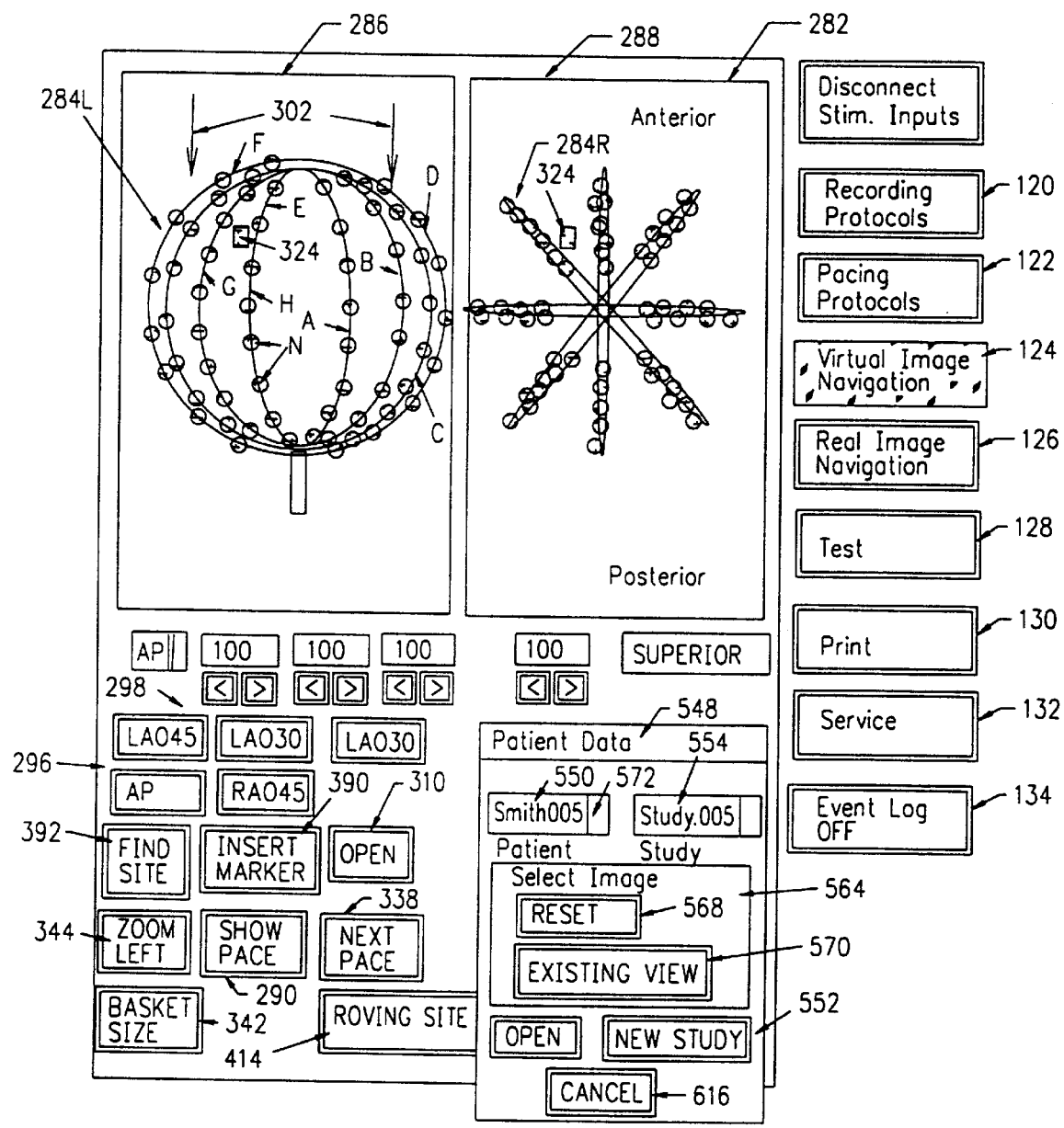
FIG. 29 is a depiction of the virtual image navigation screen of the GUI, with the Patient Data Base function enabled and the Select Image dialog box opened for data input.

When the New Study button 552 is selected, the function F2 opens an image selection dialog box 564 (see FIG. 29). The dialog box 564 prompts the physician to set the idealized image viewing angles.

Selecting the Reset button 568 starts the new study with default idealized image views in the left and right panels 286 and 288(which is the same function as the Reset View button 312 on the Toolbar 296, as shown in FIG. 9). Once the new study is underway, the physician can proceed to customize the default left and right panel images 284L/R, as previously described.

Alternatively, selecting the Existing View button 570 in the image selection box 564 starts the new study with the same markers, binary maps, features, comments, sensitivity threshold, and views active in the immediately preceding study. This option allows the physician to quickly switch among different diagnostic or therapeutic protocols (each constituting a "study") on the same patient using the same structure 58 in the same heart chamber.

Once the view is selected, the dialog box 564 and Data Window 548 are dismissed, and control returns to the navigation window 282 (FIG. 9). The new study commences, with the selected image views displayed in the navigation window 282.

During the new study, the physician can call upon all the features of the applications A1 to A7 and function F1 as already described. For example, the physician can set up binary maps, in the manner previously described (see FIGS. 11 and 12), or mark anatomic features (see FIG. 13). The physician can set up markers 404 and comment windows 406 in association with the selected image views, as FIG. 19 shows. In the comment windows 406, the physician can include further information identifying the procedure, diagnostic information, therapeutic information, or otherwise annotate the image 284L/R.

By clicking the SAVE button 314 on the Toolbar 296 at desired times, the entire graphical display, including the idealized image 284L/R, markers 406, and associated comment windows 406 are saved as a data file in the patient/study subdirectory, uniquely associated with the particular study and particular patient for storage, retrieval, or manipulation.

b. Manipulating Patient Data Base Information

Figure 30:
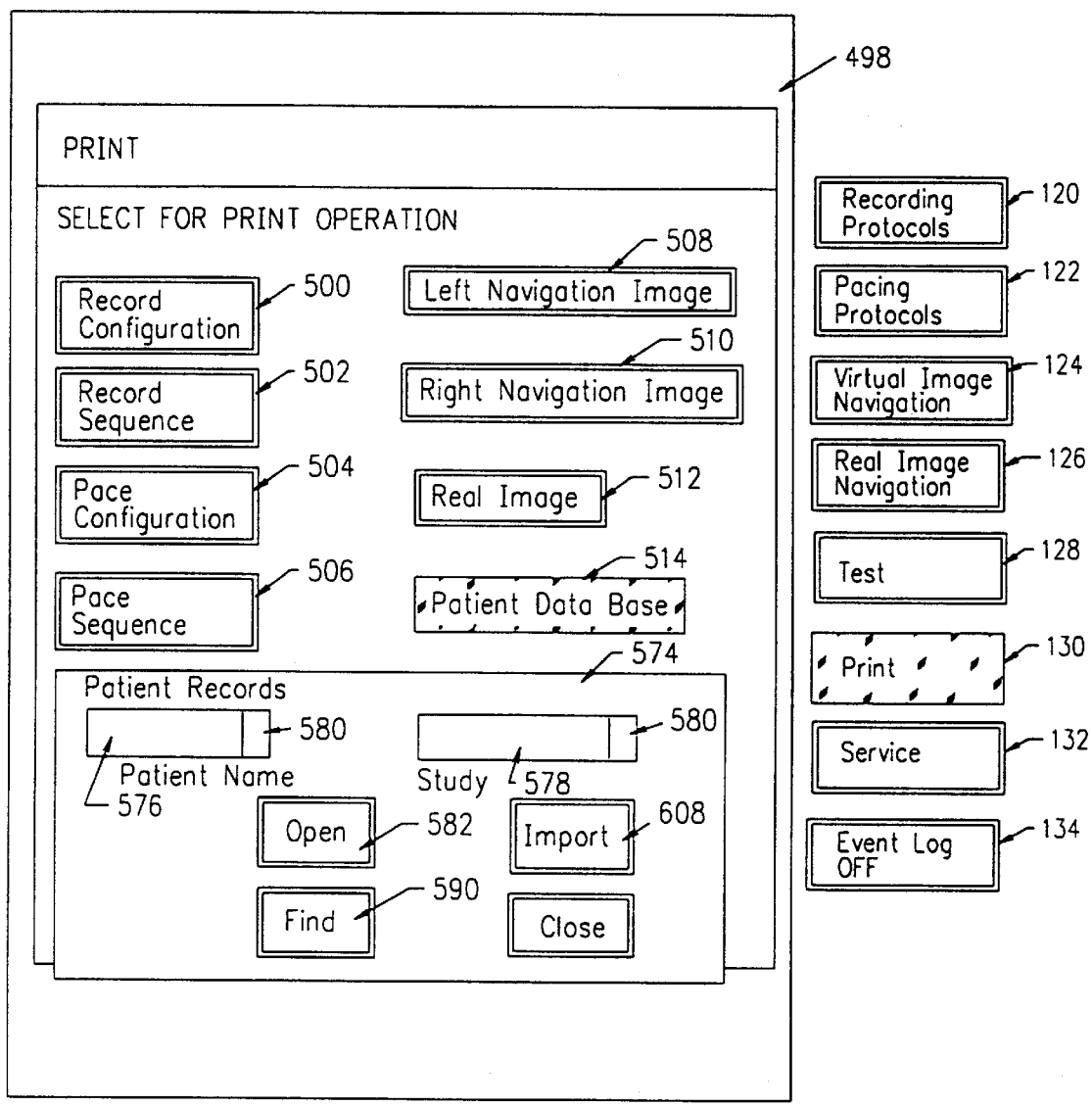
FIG. 30 is a depiction of the print screen of the GUI, with the Patient Data Base control button selected to open the Patient Records dialog box.

In the illustrated embodiment, selection of the Patient Data Base button 514 in the print window 498 (FIG. 25) opens a patient record dialog box 574 (see FIG. 30). The dialog box 574 includes a Patient Name field 576 and a Study field 578, in which the operator can specify a particular subdirectory. The fields 576 and 578 each include a menu control button 580, which, when selected, opens a drop down menu listing patient names and studies residing in the data base 32.

Figure 31:
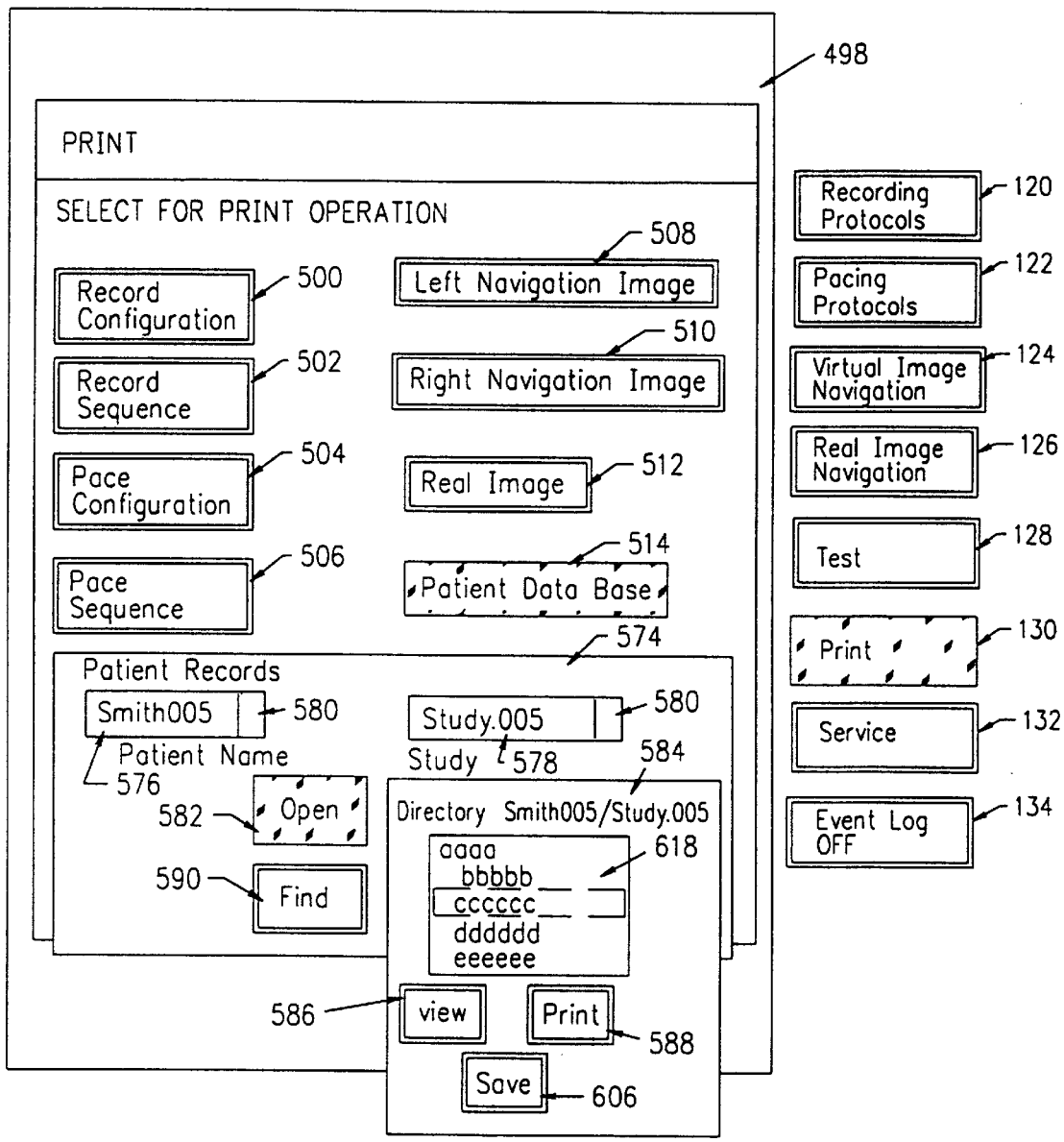
FIG. 31 is a depiction of the print screen of the GUI, with the Patient Data Base control button selected and the Directory dialog box opened.

Selection of the Open button 582 opens a directory box 584 (see FIG. 31), which list the files 618 contained in the specified subdirectory. The highlighted file can be opened for viewing (by selecting the View button 586); or printed (by selecting the Print button 588); or saved (by selecting the Save button 606).

Figure 32:
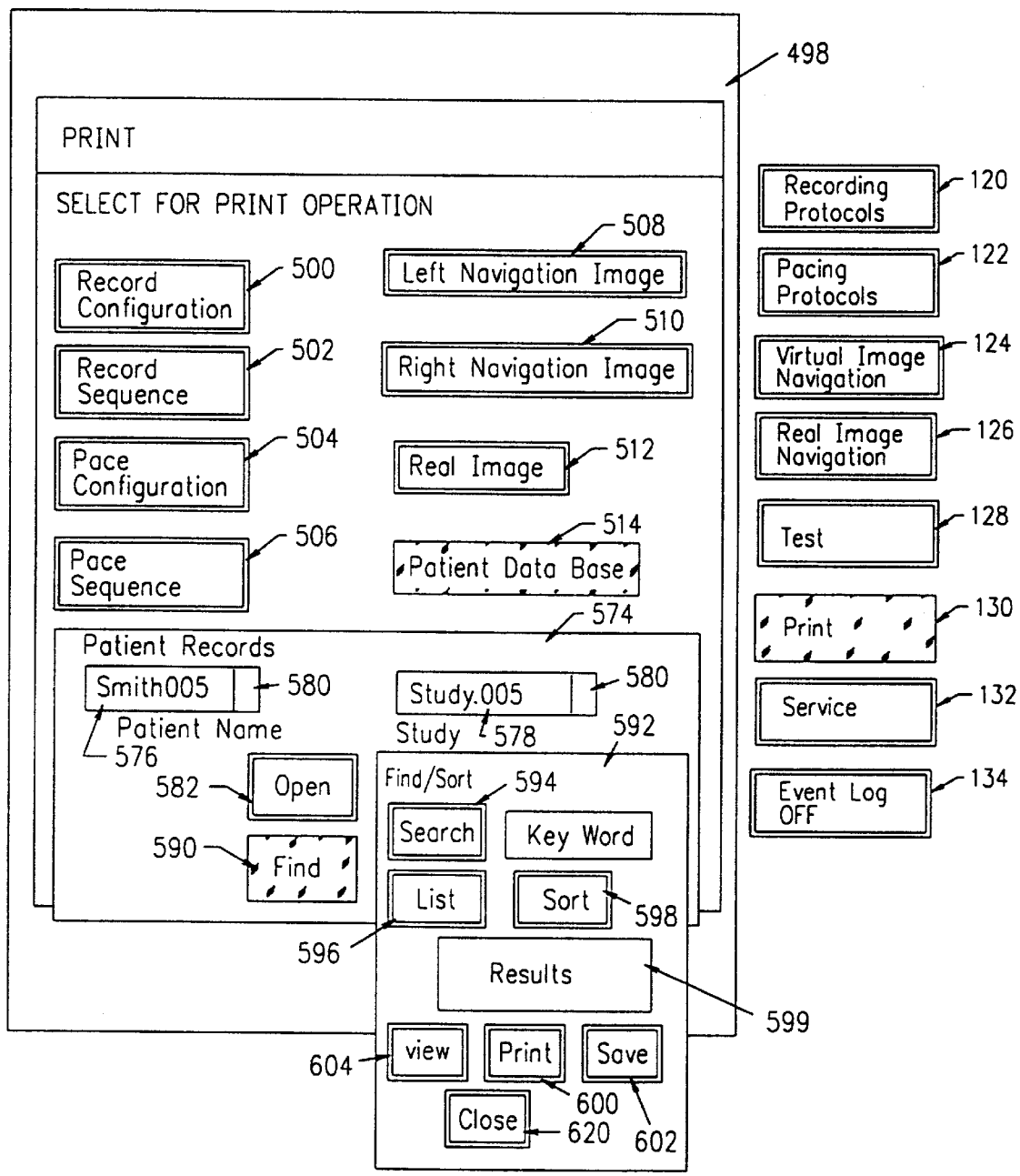
FIG. 32 is a depiction of the print screen of the GUI, with the Patient Data Base control button selected and the Find/Sort dialog box opened.

Alternatively, selecting the Find button 590 in the window 576 (see FIG. 30) opens a Find/Sort box 592 (see FIG. 32). The Find/Sort box 592 provides access to special functions that compile, search, manipulated, or filter the records in the patient data base 52 in conventional ways, e.g., by use of a SEARCH DATA BASE control button 594 (which allows key-word or file searching), a LIST DATA BASE control button 596 (which lists data base files in established directory and subdirectory order), and a SORT DATA BASE 598 control button (which allows files be arranged, e.g., chronologically, by file type, etc.). The results of the requested function are displayed for viewing in a Results field 598, which can be opened for viewing (by selecting the View button 604); or printed (by selecting the Print button 600); or saved (by selecting the Save button 602). Selecting the Close button 620 dismisses the Find/Sort box 592 and returns control to the Patient Records window 574 (see FIG. 30). Selecting the close button 622 in the Patient Records Window 574 dismisses the window 574 and return control to the print selection window 498 (as shown in FIG. 25).

As FIG. 1 shows, a communications link 610 allows patient record information to be transmitted from the hard drive 32 to a central data storage station 612. A network 614 of local or remote systems 10, 10(A), 10(B), and 10(C), each having all or some of the features described for system 10, can be linked to the central data storage station 612, by an Internet-type network, or by an intranet-type network. The network 614, all linked to the central data storage station 612, allows patient-specific data base records for many patients at one or more treatment facilities to be maintained at a single location for storage, retrieval, or manipulation. In the illustrated embodiment (see FIG. 30), the patient record dialog box also includes an IMPORT control button 608. When selected, the button 608 allows patient/study data base files residing on the station 612 to be up loaded into the patient data base 32 resident on the system 10. Conversely, the various save functions in the directory box 584 (see FIG. 31) or the Find/Sort box 592 (see FIG. 32) can specify down loading patient/study data base files from the MPU 28 to the central data storage station 612.

Various features of the invention are set forth in the following claims.

We claim:

1. An interface for association with an electrode structure which, in use, is deployed in contact with heart tissue to perform a diagnostic or therapeutic procedure, the interface comprising:

a display screen, and an interface manager coupled to the display screen and including a first function to generate a real image of the electrode structure acquired by an imaging device, a second function to generate an idealized image of the electrode structure based at least in part upon the real image, and a third function to display a view image comprising the real image of the electrode structure next to the idealized image of the electrode structure.

2. An interface according to claim 1 wherein the interface manager includes a menu function to select among display of the real image, or display of the idealized image, or both on the display screen.

3. An interface according to claim 1, wherein the third function includes a function to manually add an annotation to the image of the electrode structure on the display the annotation selected from the group consisting of an identifier, a marker and an associated text comment.

4. An interface according to claim 3 wherein the interface manager includes a file manager function to store, retrieve, or manipulate the annotated view image as a file record.

5. An interface according to claim 1 wherein the interface manager includes a file manager function to store, retrieve, or manipulate the either the real image, or the idealized image, or both as a file record.

6. An interface according to claim 1 wherein the third function includes a navigation function that generates on the display screen an output in association with the view image, showing location of a roving element, deployed in the patient, relative to the electrode structure.

7. An interface according to claim 6 wherein the navigation function generates the output based at least in part upon a real image of the roving electrode acquired by an imaging device.

8. An interface according to claim 1 wherein the third function includes a navigation function that generates on the display screen a proximity-indicating output in association with the view image, showing the proximity of a roving element, deployed in the patient, to the electrode structure.

9. An interface according to claim 8 wherein the navigation function generates the proximity-indicating output based at least in part upon a real image of the roving electrode acquired by an imaging device.

10. An interface according to claim 1 wherein the interface manager includes an input to receive patient data identifying the patient and an output to process patient data as a data base record for storage, retrieval, or manipulation.

11. An interface according to claim 10 wherein the output processes data relating to the real image, or the idealized image, or the view image in association with the patient data.

12. An interface according to claim 1, wherein the view image is a split-screen image with the real image of the electrode structure separate from the idealized image of the electrode structure.

13. An interface according to claim 12, wherein the split-screen image includes a left panel and a right panel and the real image of the electrode structure is in one of the panels and the idealized image of the electrode structure is in the other panel.

14. A method for examining myocardial tissue comprising the steps of:

deploying an electrode structure in contact with myocardial tissue, generating an idealized graphical image of the electrode structure based at least in part upon the real image, displaying a view image of the electrode structure comprising the real image of the electrode structure next to the idealized image of the electrode structure on a display screen, and causing the electrode structure to conduct a diagnostic or therapeutic procedure affecting myocardial tissue while the view image is displayed on the display screen.

15. A method according to claim 14 and further including the step of ablating myocardial tissue.

16. A method according to claim 14 and further including the step of manually altering the geometrical appearance of the view image.

17. A method according to claim 14 and further including the step of altering an operating condition of the electrode structure in response to operator input.

18. A method according to claim 14, wherein the view image is a split-screen image with the real image of the electrode structure separate from the idealized image of the electrode structure.

19. A method according to claim 18, wherein the split-screen image includes a left panel and a right panel and the real image of the electrode structure is in one of the panels and the idealized image of the electrode structure is in the other panel.

* * * * *

UNITED STATES PATENT AND TRADEMARK OFFICE
CERTIFICATE OF CORRECTION

PATENT NO.    : 6,192,266 B1
DATED         : February 20, 2001
INVENTOR(S)   : Daniel A. Dupree, Tuan Nguyen, Dorin Panescu and James G. Whayne It is certified that error appears in the above-identified patent and that said Letters Patent is hereby corrected as shown below:

Column 12,
Line 26, delete "CONSTELLATIONS" and insert therefor -- CONSTELLATION® --

Column 27,
Line 45, delete "(AS)" and insert therefor -- (A5) --

Signed and Sealed this

Twenty-fourth Day of September, 2002

Attest:

JAMES E. ROGAN
*Attesting Officer*        *Director of the United States Patent and Trademark Office*